US011278397B2

(12) United States Patent
Quill et al.

(10) Patent No.: US 11,278,397 B2
(45) Date of Patent: Mar. 22, 2022

(54) HEART VALVE PROSTHESES HAVING MULTIPLE SUPPORT ARMS AND METHODS FOR PERCUTANEOUS HEART VALVE REPLACEMENT

(71) Applicant: Medtronic, Inc., Minneapolis, MN (US)

(72) Inventors: Jason Quill, Forest Lake, MN (US); Padraig Savage, Santa Rosa, CA (US); Joshua Dwork, Santa Rosa, CA (US); Kshitija Garde, Fullerton, CA (US); Sarah Ahlberg, Maple Grove, MN (US); Igor Kovalsky, Minnetonka, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 0 days.

(21) Appl. No.: 16/403,769

(22) Filed: May 6, 2019

(65) Prior Publication Data

US 2019/0254818 A1    Aug. 22, 2019

Related U.S. Application Data

(62) Division of application No. 15/012,533, filed on Feb. 1, 2016, now Pat. No. 10,321,992.

(51) Int. Cl.
    *A61F 2/24* (2006.01)
(52) U.S. Cl.
    CPC .......... *A61F 2/2418* (2013.01); *A61F 2/2427* (2013.01); *A61F 2230/001* (2013.01); *A61F 2230/005* (2013.01); *A61F 2250/0037* (2013.01)

(58) Field of Classification Search
    CPC .......... A61F 2/2418; A61F 2/2427; A61F 2/24
    See application file for complete search history.

(56) References Cited

U.S. PATENT DOCUMENTS 7,748,389 B2    7/2010    Salahieh
7,837,727 B2    11/2010   Goetz et al.
(Continued)

FOREIGN PATENT DOCUMENTS

CN            104302247 A     1/2015

OTHER PUBLICATIONS

PCT/US2017/015627, The International Search Report and the Written Opinion of the International Searching Authority, dated May 4, 2017.

*Primary Examiner* — Christopher D. Prone
(74) *Attorney, Agent, or Firm* — Medler Ferro Woodhouse & Mills PLLC

(57) ABSTRACT

Prosthetic heart valve devices and associated methods for percutaneous or transcatheter heart valve replacement are disclosed herein. A heart valve prosthesis configured in accordance herewith includes a frame having a valve support and a plurality of support arms extending therefrom. The plurality of support arms may include a main support arm configured to extend from the valve support for capturing at least a portion of a valve leaflet of a native heart valve therebetween when the valve prosthesis is in an expanded configuration and deployed within the native heart valve. In addition, the plurality of support arms may include multiple supplemental support arms disposed about the circumference of the valve support that when deployed in the expanded configuration are configured to at least partially engage subannular tissue at the native heart valve.

20 Claims, 14 Drawing Sheets

(56) References Cited

U.S. PATENT DOCUMENTS

| | | |
|---|---|---|
| 7,896,915 B2 | 3/2011 | Guyenot et al. |
| 7,914,575 B2 | 3/2011 | Guyenot et al. |
| 7,947,075 B2 | 5/2011 | Goetz et al. |
| 7,972,378 B2 | 7/2011 | Tabor et al. |
| 8,052,749 B2 | 11/2011 | Salahieh |
| 8,343,213 B2 | 1/2013 | Salahieh |
| 8,348,995 B2 | 1/2013 | Tuval et al. |
| 8,348,996 B2 | 1/2013 | Tuval et al. |
| 8,366,767 B2 | 2/2013 | Zhang |
| 8,366,768 B2 | 2/2013 | Zhang |
| 8,414,643 B2 | 4/2013 | Tuval et al. |
| 8,444,689 B2 | 5/2013 | Zhang |
| 8,449,599 B2 | 5/2013 | Chau et al. |
| 8,540,767 B2 | 9/2013 | Zhang |
| 8,579,964 B2 | 11/2013 | Lane et al. |
| 8,579,965 B2 | 11/2013 | Bonhoeffer |
| 8,585,755 B2 | 11/2013 | Chau et al. |
| 8,673,000 B2 | 3/2014 | Tabor et al. |
| 8,728,155 B2 | 5/2014 | Montorfano et al. |
| 8,747,460 B2 | 6/2014 | Tuval et al. |
| 8,771,345 B2 | 7/2014 | Tuval et al. |
| 8,771,346 B2 | 7/2014 | Tuval et al. |
| 8,784,481 B2 | 7/2014 | Alkhatib et al. |
| 8,834,563 B2 | 9/2014 | Righini |
| 8,834,564 B2 | 9/2014 | Tuval |
| 8,840,661 B2 | 9/2014 | Manasse |
| 8,876,894 B2 | 11/2014 | Tuval et al. |
| 8,876,895 B2 | 11/2014 | Tuval et al. |
| 8,926,691 B2 | 1/2015 | Chau et al. |
| 8,956,404 B2 | 2/2015 | Bortlein et al. |
| 8,986,373 B2 | 3/2015 | Chau et al. |
| 8,992,604 B2 | 3/2015 | Gross et al. |
| 2003/0036791 A1 | 2/2003 | Bonhoeffer |
| 2006/0224183 A1* | 10/2006 | Freudenthal ..... A61B 17/12109 606/213 |
| 2010/0131054 A1 | 5/2010 | Tuval et al. |
| 2010/0137979 A1 | 6/2010 | Tuval et al. |
| 2011/0208297 A1 | 8/2011 | Tuval et al. |
| 2011/0208298 A1 | 8/2011 | Tuval et al. |
| 2011/0224785 A1 | 9/2011 | Hacohen |
| 2012/0022640 A1 | 1/2012 | Gross et al. |
| 2012/0035722 A1 | 2/2012 | Tuval |
| 2012/0053682 A1 | 3/2012 | Kovalsky et al. |
| 2012/0185039 A1 | 7/2012 | Tuval et al. |
| 2012/0303116 A1* | 11/2012 | Gorman, III .......... A61F 2/2418 623/2.11 |
| 2013/0116779 A1 | 5/2013 | Weber |
| 2013/0172992 A1 | 7/2013 | Gross et al. |
| 2013/0190861 A1 | 7/2013 | Chau et al. |
| 2013/0211508 A1 | 8/2013 | Lane et al. |
| 2013/0310928 A1 | 11/2013 | Morriss et al. |
| 2014/0018906 A1 | 1/2014 | Rafiee |
| 2014/0039611 A1 | 2/2014 | Lane et al. |
| 2014/0039613 A1 | 2/2014 | Navia et al. |
| 2014/0046434 A1 | 2/2014 | Rolando et al. |
| 2014/0052237 A1 | 2/2014 | Lane et al. |
| 2014/0052240 A1 | 2/2014 | Zhang |
| 2014/0088695 A1 | 3/2014 | Figulla |
| 2014/0088696 A1 | 3/2014 | Figulla et al. |
| 2014/0121763 A1 | 5/2014 | Duffy et al. |
| 2014/0155997 A1 | 6/2014 | Braido |
| 2014/0194892 A1 | 7/2014 | Kovalsky et al. |
| 2014/0194982 A1 | 7/2014 | Kovalsky et al. |
| 2014/0194983 A1 | 7/2014 | Kovalsky et al. |
| 2014/0207231 A1 | 7/2014 | Hacohen et al. |
| 2014/0222136 A1 | 8/2014 | Geist et al. |
| 2014/0222142 A1 | 8/2014 | Kovalsky et al. |
| 2014/0228946 A1 | 8/2014 | Chau et al. |
| 2014/0236292 A1 | 8/2014 | Braido |
| 2014/0249622 A1 | 9/2014 | Carmi et al. |
| 2014/0257467 A1 | 9/2014 | Lane et al. |
| 2014/0277390 A1 | 9/2014 | Ratz et al. |
| 2014/0277409 A1 | 9/2014 | Bortlein et al. |
| 2014/0277410 A1 | 9/2014 | Bortlein et al. |
| 2014/0277411 A1 | 9/2014 | Bortlein et al. |
| 2014/0324164 A1 | 10/2014 | Gross et al. |
| 2014/0343669 A1 | 11/2014 | Lane et al. |
| 2014/0350669 A1 | 11/2014 | Gillespie et al. |
| 2014/0371844 A1 | 12/2014 | Dale et al. |
| 2015/0018944 A1 | 1/2015 | O'Connell et al. |
| 2015/0073540 A1 | 3/2015 | Salahieh |
| 2015/0073541 A1 | 3/2015 | Salahieh |
| 2015/0081013 A1 | 3/2015 | Braido et al. |
| 2015/0181013 A1 | 3/2015 | Braido et al. |
| 2015/0119982 A1 | 4/2015 | Quill et al. |
| 2015/0328000 A1 | 11/2015 | Ratz et al. |
| 2015/0351904 A1 | 12/2015 | Cooper et al. |

* cited by examiner

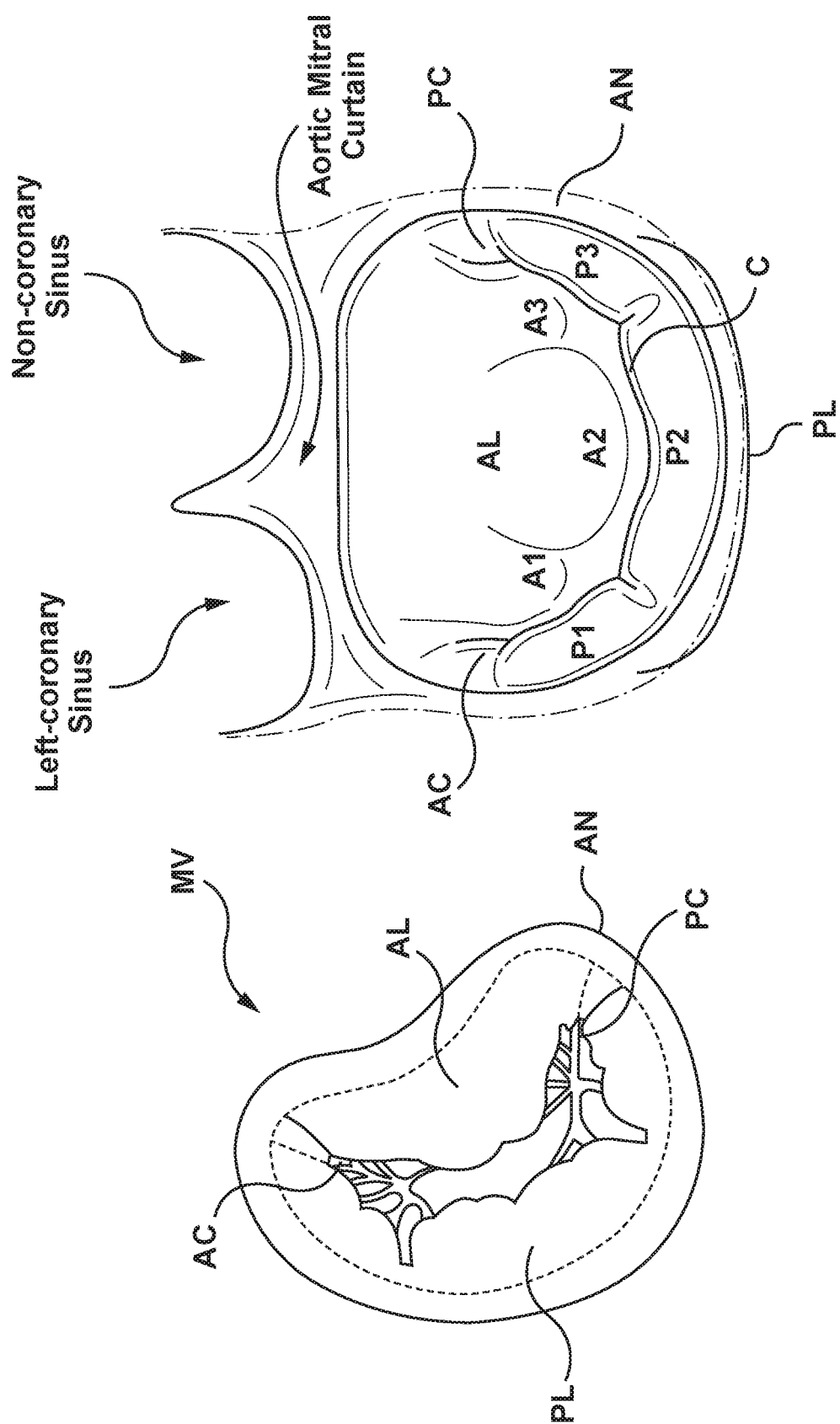

HEART VALVE PROSTHESES HAVING MULTIPLE SUPPORT ARMS AND METHODS FOR PERCUTANEOUS HEART VALVE REPLACEMENT

CROSS-REFERENCE TO RELATED APPLICATION

This application is a divisional of U.S. application Ser. No. 15/012,533 filed Feb. 1, 2016, issued as U.S. Pat. No. 10,321,992, the disclosure of which is incorporated by reference herein in its entirety.

FIELD OF THE INVENTION

The present technology relates generally to heart valve prostheses and associated methods. In particular, several embodiments are directed to transcatheter heart valve devices having multiple support arms for percutaneous replacement of native heart valves, such as a mitral valve.

BACKGROUND OF THE INVENTION

The human heart is a four chambered, muscular organ that provides blood circulation through the body during a cardiac cycle. The four main chambers include the right atria and right ventricle which supplies the pulmonary circulation, and the left atria and left ventricle which supplies oxygenated blood received from the lungs to the remaining body. To insure that blood flows in one direction through the heart, atrioventricular valves (tricuspid and mitral valves) are present between the junctions of the atria and the ventricles, and semi-lunar valves (pulmonary valve and aortic valve) govern the exits of the ventricles leading to the lungs and the rest of the body. These valves contain leaflets that open and shut in response to blood pressure changes caused by the contraction and relaxation of the heart chambers. The leaflets move apart from each other to open and allow blood to flow downstream of the valve, and coapt to close and prevent backflow or regurgitation in an upstream manner.

Diseases associated with heart valves, such as those caused by damage or a defect, can include stenosis and valvular insufficiency or regurgitation. For example, valvular stenosis causes the valve to become narrowed and hardened which can prevent blood flow to a downstream heart chamber to occur at the proper flow rate and cause the heart to work harder to pump the blood through the diseased valve. Valvular insufficiency or regurgitation occurs when the valve does not close completely, allowing blood to flow backwards, thereby causing the heart to be less efficient. A diseased or damaged valve, which can be congenital, age-related, drug-induced, or in some instances, caused by infection, can result in an enlarged, thickened heart that loses elasticity and efficiency. Some symptoms of heart valve diseases can include weakness, shortness of breath, dizziness, fainting, palpitations, anemia and edema, and blood clots which can increase the likelihood of stroke or pulmonary embolism. Symptoms can often be severe enough to be debilitating and/or life threatening.

Prosthetic heart valves have been developed for repair and replacement of diseased and/or damaged heart valves. Such valves can be percutaneously delivered and deployed at the site of the diseased heart valve through catheter-based systems. Such prosthetic heart valves can be delivered while in a low-profile or compressed/contracted arrangement so that the prosthetic valves can be contained within a sheath component of a delivery catheter and advanced through the patient's vasculature. Once positioned at the treatment site, the prosthetic valves can be expanded to engage tissue at the diseased heart valve region to, for instance, hold the prosthetic valve in position. While these prosthetic valves offer minimally invasive methods for heart valve repair and/or replacement, challenges remain to provide prosthetic valves that prevent leakage between the implanted prosthetic valve and the surrounding tissue (paravalvular leakage) and for preventing movement and/or migration of the prosthetic valve that could occur during the cardiac cycle. For example, the mitral valve presents numerous challenges, such as prosthetic valve dislodgement or improper placement due to the presence of chordae tendinae and remnant leaflets, leading to valve impingement. Additional challenges can include providing a prosthetic valve that resists pre-mature failure of various components that can occur when subjected to the distorting forces imparted by the native anatomy and during the cardiac cycle. Further anatomical challenges associated with treatment of a mitral valve include providing a prosthetic valve to accommodate the kidney shape of the annulus. Moreover, the annulus has muscle only along the exterior wall of the valve with only a thin vessel wall that separates the mitral valve and the aortic valve. This anatomical muscle distribution, along with the high pressures experienced on the left ventricular contraction, can be problematic for mitral valve prosthesis.

BRIEF SUMMARY OF THE INVENTION

Embodiments hereof are directed to heart valve prostheses having multiple support arms and methods of percutaneous implantation thereof. The heart valve prosthesis has a compressed delivery configuration and an expanded deployed configuration for deployment within a native heart valve or a prior implanted prosthetic heart valve. The valve prosthesis includes a frame having a tubular portion for retaining a prosthetic valve component therein, the tubular portion having a first end and a second end. An inflow portion of the frame radially extends from the first end of the tubular or conical portion when the valve prosthesis is in the expanded configuration. A main support arm of the frame extends from the second end of the tubular portion and has a first length. A first set of supplemental support arms of the frame also extend from the second end of the tubular portion and each of the first set of supplemental support arms has a second length. A second set of supplemental support arms of the frame also extend from the second end of the tubular portion and each of the second set of supplemental support arms has a third length that is less than the second length. In embodiment hereof, a first length of the main support arm is longer than the respective second and third lengths of the supplemental support arms in the first and second sets of supplemental support arms.

In another embodiment, a heart valve prosthesis has a compressed delivery configuration and an expanded deployed configuration for deployment within a heart. The valve prosthesis has a frame that defines a valve support having a first end and a second end, and that defines an inflow portion that radially extends from the first end of the valve support when the valve prosthesis is in the expanded configuration. The frame further defines and/or includes a main support arm extending from the second end of the valve support, a plurality of tall supplemental support arms extending from the second end of the valve support, and a plurality of short supplemental support arms extending from the second end of the valve support, wherein the main support arm is longer than the pluralities of tall and short supplemental support arms. In embodiments hereof, when the valve prosthesis is in the expanded configuration the main support arm, the plurality of tall supplemental support arms and the plurality of short supplemental support arms bend toward the first end of the valve support, and each of the plurality of tall supplemental support arms and each of the plurality of short supplemental support arms has substantially the same deployed height.

Further aspects of the present technology are directed to methods of deploying a valve prosthesis having a compressed configuration for delivery to a treatment site and an expanded configuration for deployment within a heart. In one embodiment, a method can include providing transatrial access to a left atrium of the heart and advancing a distal portion of a delivery catheter having the valve prosthesis in the compressed configuration therein into the left atrium via the transatrial access. The valve prosthesis can include a frame having a main support arm and a plurality of supplemental support arms. The method can also include deploying within the left atrium the main support arm and the plurality of supplemental support arms of the valve prosthesis such that each of the main support arm and the plurality of supplemental support arms assumes a bent deployed state as it extends from the distal portion of the delivery catheter. The method can further include advancing the distal portion of the delivery catheter toward an annulus of a native mitral valve of the heart until the main support arm and the plurality of supplemental support arms in the bent deployed state are pushed through the annulus and into a left ventricle of the heart. The method can still further include proximally retracting or pulling the delivery catheter until each of the main support arm and the plurality of supplemental support arms engages at least a portion of anterior, posterior leaflets, and/or the native annulus of the native mitral valve, and deploying a remainder of the valve prosthesis from the delivery catheter to replace the native mitral valve.

BRIEF DESCRIPTION OF DRAWINGS

The foregoing and other features and aspects of the present technology can be better understood from the following description of embodiments and as illustrated in the accompanying drawings. The accompanying drawings, which are incorporated herein and form a part of the specification, further serve to illustrate the principles of the present technology. The components in the drawings are not necessarily to scale.

FIG. 3A is a schematic illustration of a superior view a mitral valve isolated from the surrounding heart structures and showing the annulus and native leaflets.

FIG. 3B is a schematic illustration of a superior view a mitral valve, aortic mitral curtain and portions of the aortic valve isolated from the surrounding heart structures and showing regions of the native mitral valve leaflets.

DETAILED DESCRIPTION OF THE INVENTION

Specific embodiments of the present technology are now described with reference to the figures, wherein like reference numbers indicate identical or functionally similar elements. The terms "distal" and "proximal" are used in the following description with respect to a position or direction relative to the treating clinician or with respect to a prosthetic heart valve device. For example, "distal" or "distally" are a position distant from or in a direction away from the clinician when referring to delivery procedures or along a vasculature. Likewise, "proximal" and "proximally" are a position near or in a direction toward the clinician. With respect to a prosthetic heart valve device, the terms "proximal" and "distal" can refer to the location of portions of the device with respect to the direction of blood flow. For example, "proximal" can refer to an upstream position or a position of blood inflow, and "distal" can refer to a downstream position or a position of blood outflow.

The following detailed description is merely exemplary in nature and is not intended to limit the present technology or the application and uses of the present technology. Although the description of embodiments hereof are in the context of treatment of heart valves and particularly a mitral valve, the present technology may also be used in any other body passageways where it is deemed useful. Furthermore, there is no intention to be bound by any expressed or implied theory presented in the preceding technical field, background, brief summary or the following detailed description.

Embodiments of the present technology as described herein can be combined in many ways to treat one or more of many valves of the body including valves of the heart such as the mitral or tricuspid valve. The embodiments of the present technology can be therapeutically combined with many known surgeries and procedures, for example, such embodiments can be combined with known methods of accessing the valves of the heart such as the mitral valve with antegrade approaches, such as a transseptal or transatrial approach, and combinations thereof.

Figure 1:
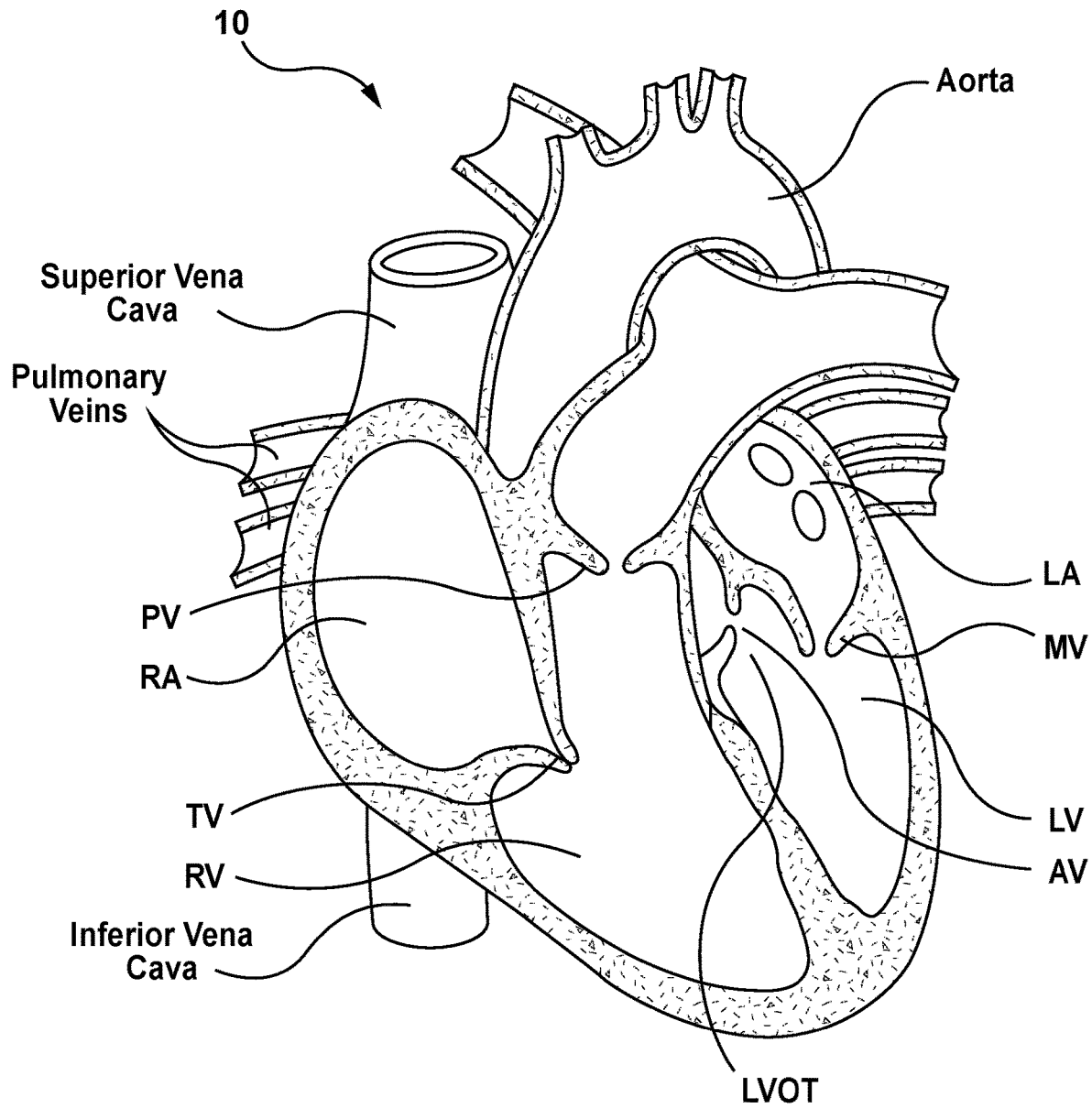
FIG. 1 is a schematic sectional illustration of a mammalian heart having native valve structures.
Figure 2A:
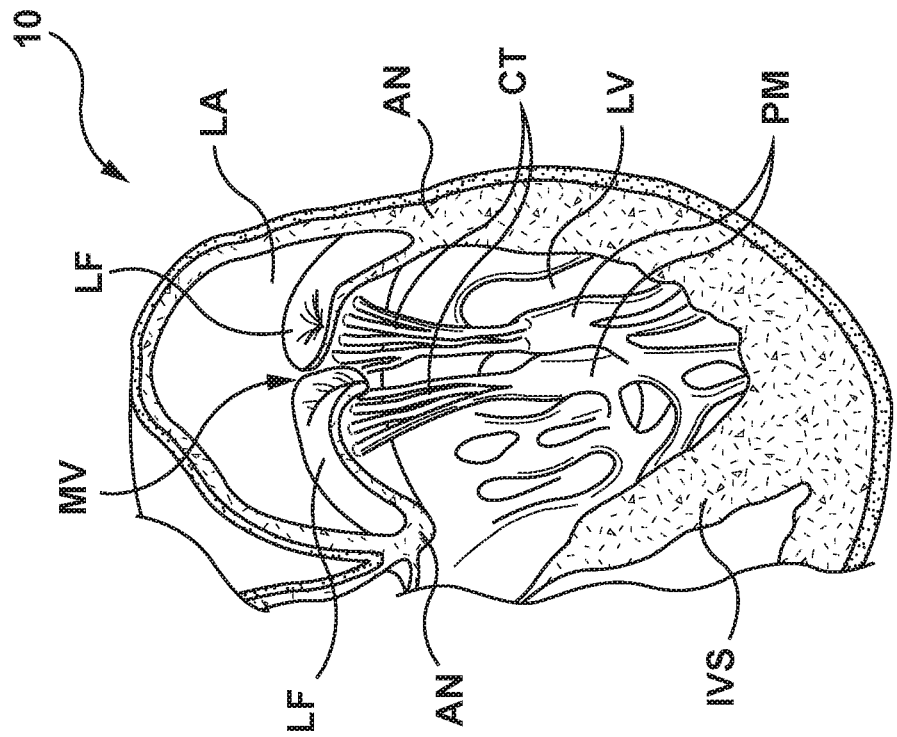
FIG. 2A is a schematic sectional illustration of a left ventricle of a mammalian heart showing anatomical structures and a native mitral valve.

FIG. 1 is a schematic sectional illustration of a mammalian heart 10 that depicts the four heart chambers (right atria RA, right ventricle RV, left atria LA, left ventricle LV) and native valve structures (tricuspid valve TV, mitral valve MV, pulmonary valve PV, aortic valve AV). FIG. 2A is a schematic sectional illustration of a left ventricle LV of a mammalian heart 10 showing anatomical structures and a native mitral valve MV. Referring to FIGS. 1 and 2A together, the heart 10 comprises the left atrium LA that receives oxygenated blood from the lungs via the pulmonary veins. The left atrium LA pumps the oxygenated blood through the mitral valve MV and into the left ventricle LV during ventricular diastole. The left ventricle LV contracts during systole and blood flows outwardly through the aortic valve AV, into the aorta and to the remainder of the body.

Figure 2B:
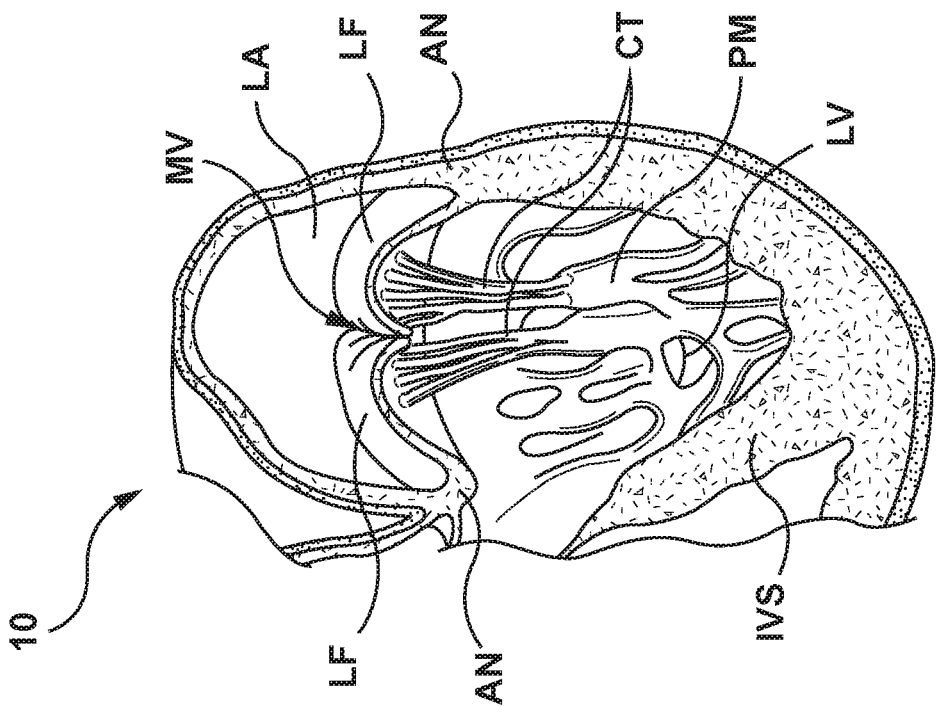
FIG. 2B is a schematic sectional illustration of the left ventricle of the heart having a prolapsed mitral valve in which the leaflets do not sufficiently coapt and which is suitable for replacement with various embodiments of prosthetic heart valves in accordance with the present technology.

In a healthy heart, the leaflets LF of the mitral valve MV meet evenly at the free edges or "coapt" to close and prevent back flow of blood during contraction of the left ventricle LV (FIG. 2A). Referring to FIG. 2A, the leaflets LF attach the surrounding heart structure via a dense fibrous ring of connective tissue called an annulus AN which is distinct from both the leaflet tissue LF as well as the adjoining muscular tissue of the heart wall. In general, the connective tissue at the annulus AN is more fibrous, tougher and stronger than leaflet tissue. The flexible leaflet tissue of the mitral leaflets LF are connected to papillary muscles PM, which extend upwardly from the lower wall of the left ventricle LV and the interventricular septum IVS, via branching tendons called chordae tendinae CT. In a heart 10 having a prolapsed mitral valve MV in which the leaflets LF do not sufficiently coapt or meet, as shown in FIG. 2B, leakage from the left atrium LA into the left ventricle LV will occur. Several structural defects can cause the mitral leaflets LF to prolapse such that regurgitation occurs, including ruptured chordae tendinae CT, impairment of papillary muscles PM (e.g., due to ischemic heart disease), and enlargement of the heart and/or mitral valve annulus AN (e.g., cardiomyopathy).

FIG. 3 is a superior view of a mitral valve MV isolated from the surrounding heart structures and further illustrating the shape and relative sizes of the mitral valve leaflets AL, PL and annulus AN. FIG. 3B is a schematic illustration of a superior view a mitral valve MV, aortic mitral curtain and portions of the aortic valve AV isolated from the surrounding heart structures and showing regions of the native mitral valve leaflets AL, PL. With reference to FIGS. 3A and 3B together, the mitral valve MV includes an anterior leaflet AL with segments or scallops A1, A2, and A3 that meet and oppose respective segments or scallops P1, P2 and P3 of a posterior leaflet PL at a coaptation line C (FIG. 3B) when closed. FIGS. 3A and 3B together further illustrate the shape and relative sizes of the leaflets AL, PL of the mitral valve. As shown, the mitral valve MV generally has a "D" or kidney-like shape and the line of coaptation C is curved or C-shaped, thereby defining a relatively large anterior leaflet AL and substantially smaller posterior leaflet PL. Both leaflets appear generally crescent-shaped from the superior or atrial side, with the anterior leaflet AL being substantially wider in the middle of the valve at the A2 segment thereof than the posterior leaflet at the P2 segment thereof (e.g., comparing segments A2 and P2, FIG. 3B). As illustrated in FIGS. 3A and 3B, at the opposing ends of the line of coaptation C, the leaflets join together at corners called the anterolateral commissure AC and posteromedial commissure PC, respectively. When the anterior leaflet AL and posterior leaflet PL fail to meet (FIG. 3A), regurgitation between the leaflets AL, PL or at commissures AC, PC at the corners between the leaflets can occur.

Referring to FIGS. 3A and 3B, the mitral valve annulus AN is a fibrotic ring that consists of an anterior part and a posterior part. The aortic-mitral curtain (FIG. 3B) is a fibrous structure that connects the anterior mitral annulus AN intimately with the aortic valve annulus (at the level of the left and non-coronary cusps or sinuses). The posterior part of the mitral annulus AN is not reinforced by other structures of the heart and is rather discontinuous (making it prone to dilatation). The leaflets AL, PL and the annulus AN are comprised of different types of cardiac tissue having varying strength, toughness, fibrosity, and flexibility. Furthermore, the mitral valve MV may also comprise a region of tissue interconnecting each leaflet to the annulus AN (indicated at dashed line in FIG. 3A).

A person of ordinary skill in the art will recognize that the dimensions and physiology of the patient may vary among patients, and although some patients may comprise differing physiology, the teachings as described herein can be adapted for use by many patients having various conditions, dimensions and shapes of the mitral valve. For example, work in relation to embodiments suggests that patients may have a long dimension across the annulus and a short dimension across the annulus with or without well-defined peak and valley portions, and the methods and device as described herein can be configured accordingly.

Embodiments of prosthetic heart valve devices and associated methods in accordance with the present technology are described in this section with reference to FIGS. 4A-11. It will be appreciated that specific elements, substructures, uses, advantages, and/or other aspects of the embodiments described herein and with reference to FIGS. 4A-11 can be suitably interchanged, substituted or otherwise configured with one another in accordance with additional embodiments of the present technology.

Provided herein are systems, devices and methods suitable for percutaneous delivery and implantation of prosthetic heart valves in a heart of a patient, wherein the prosthetic heart valves may be reference to as a transcatheter valve prosthesis. In some embodiments, methods and devices are presented for the treatment of valve disease by minimally invasive implantation of artificial or prosthetic heart valves. For example, a prosthetic heart valve device, in accordance with embodiments described herein, can be implanted for replacement of a diseased or damaged native mitral valve or prior implanted prosthetic mitral valve in a patient, such as in a patient suffering from a prolapsed mitral valve illustrated in FIG. 2A. In further embodiments, the device is suitable for implantation and replacement of other diseased or damaged heart valves or prior implanted prosthetic heart valves, such as tricuspid, pulmonary and aortic heart valves. A transcatheter valve prosthesis in accordance with embodiments hereof has a compressed configuration for delivery via a delivery catheter within a vasculature and an expanded configuration for deployment within a heart.

Figure 4A:
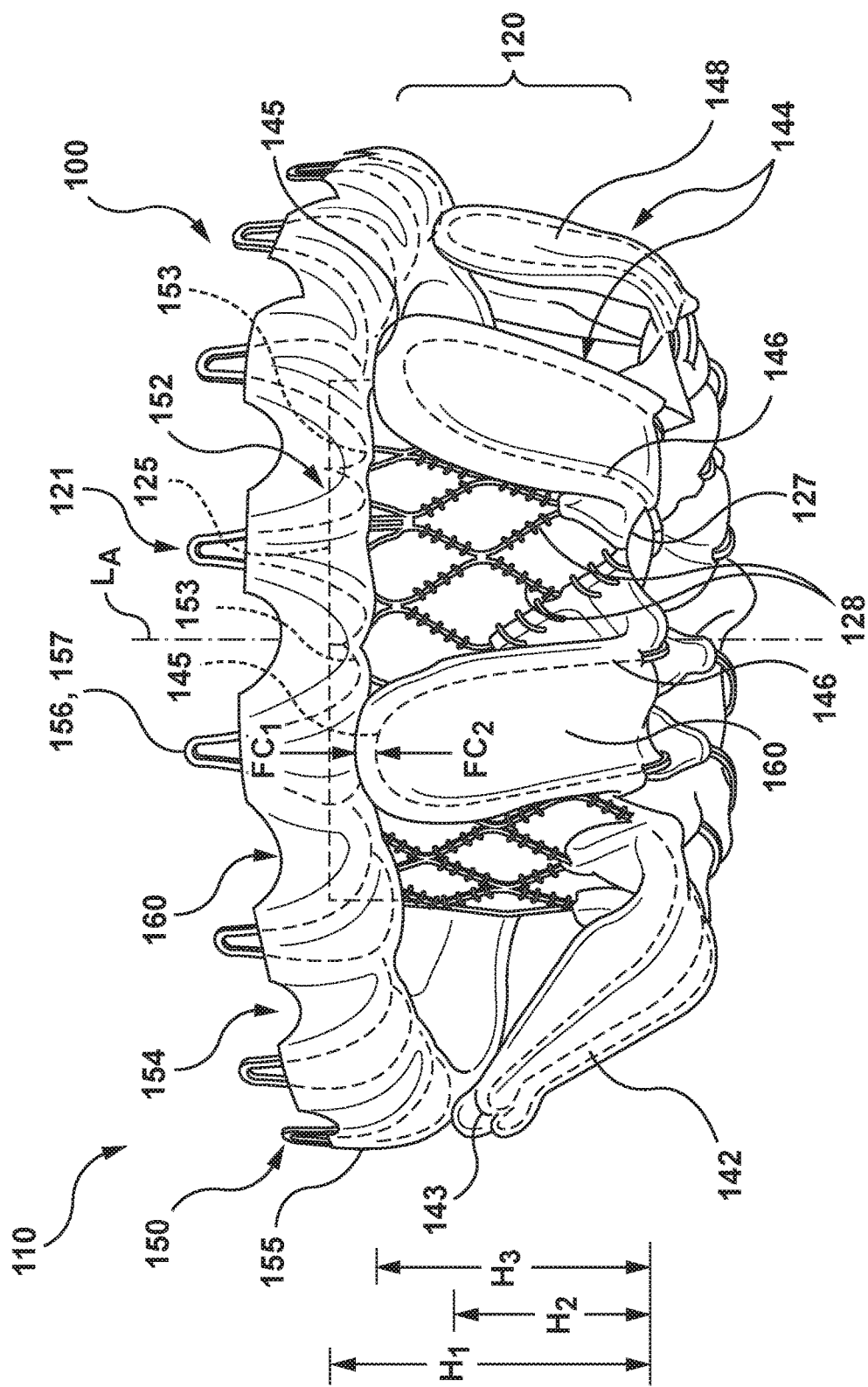
FIG. 4A is a side view of a heart valve prosthesis in a deployed or expanded configuration (e.g., a deployed state) in accordance with an embodiment of the present technology.
Figure 4B:
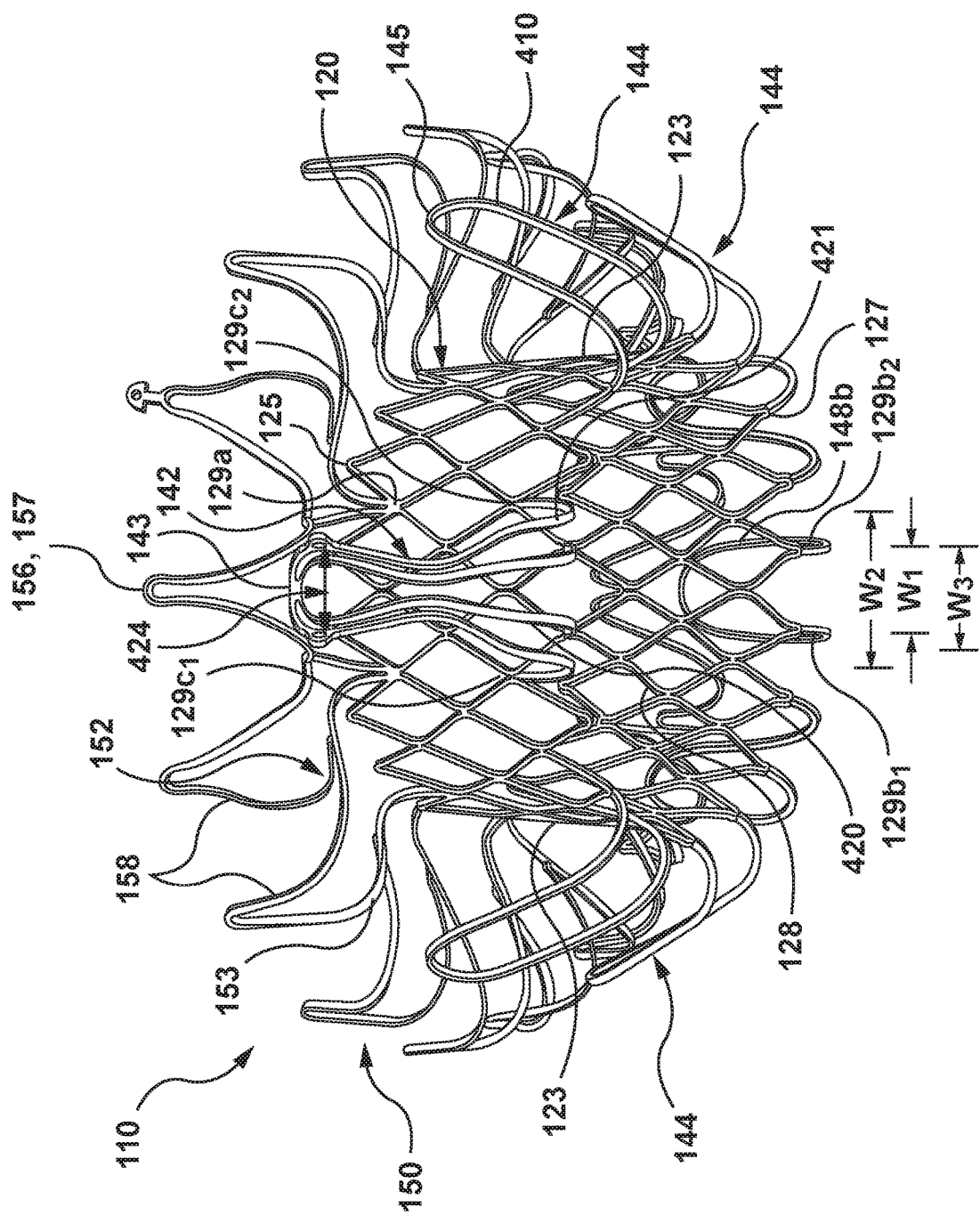
FIG. 4B is a perspective view of a frame of the heart valve prosthesis of FIG. 4A in the expanded configuration in accordance with an embodiment of the present technology.
Figure 4C:
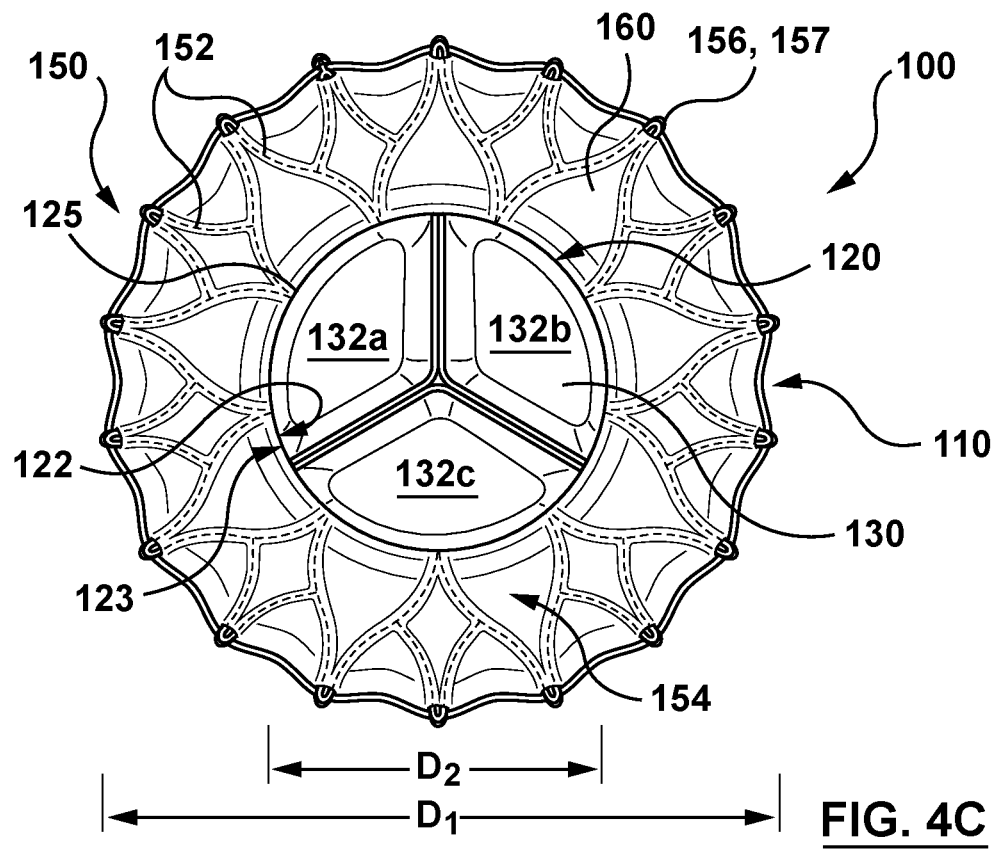
FIG. 4C is a top view of the heart valve prosthesis of FIG. 4A in the expanded configuration in accordance with an embodiment of the present technology.
Figure 4D:
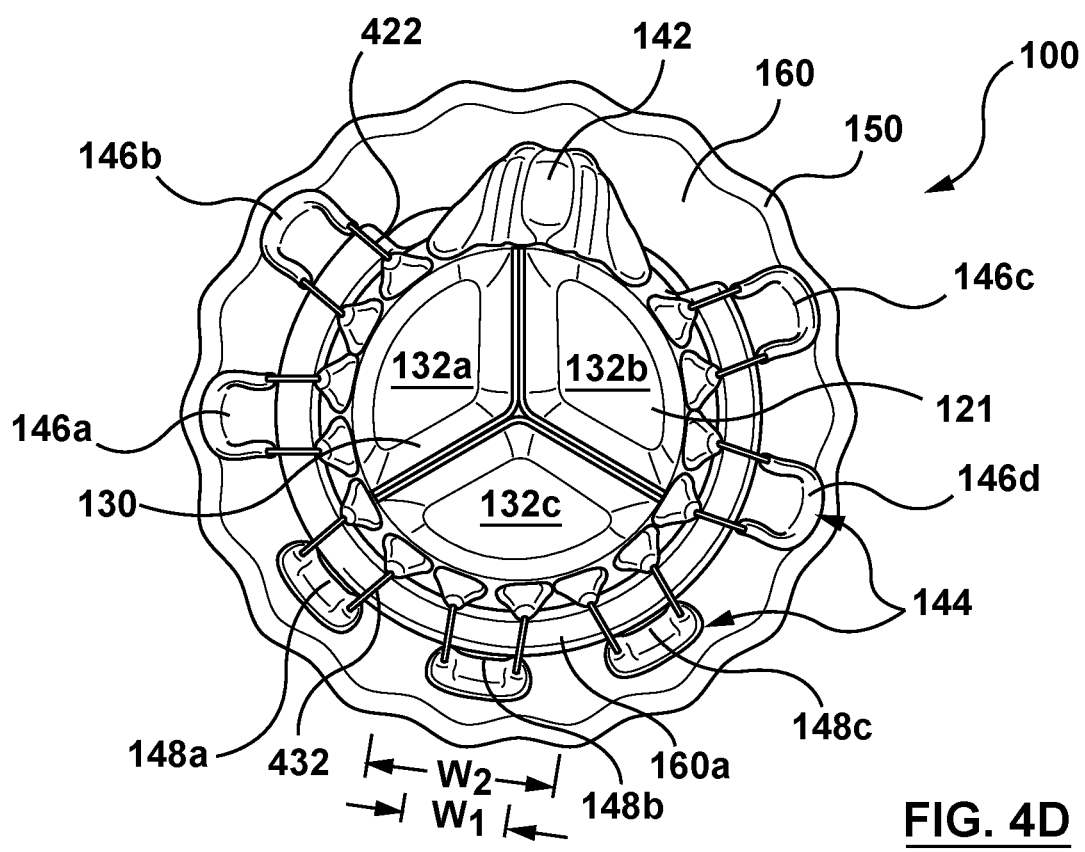
FIG. 4D is a bottom view of the heart valve prosthesis of FIGS. 4A and 4B in the expanded configuration and in accordance with an embodiment of the present technology.

FIG. 4A is a side view of a heart valve prosthesis or a prosthetic heart valve device 100 in a radially expanded configuration (e.g., a deployed state) in accordance with an embodiment of the present technology. FIG. 4B is a perspective view of a frame or stent-like support structure 110 of the heart valve prosthesis 100 of FIG. 4A in the expanded configuration in accordance with an embodiment of the present technology. FIGS. 4C and 4D are top or superior side and bottom or inferior side views, respectively, of the heart valve prosthesis 100 of FIG. 4A in the expanded configuration in accordance with an embodiment of the present technology. Referring to FIGS. 4A-4D together, the heart valve prosthesis 100 has the frame or stent-like support structure 110 that includes a tubular portion or structural valve support 120 that defines a lumen 121 for retaining, holding and/or securing a prosthetic valve component 130 (FIGS. 4C and 4D) therein. The valve support 120 can be generally cylindrical in shape having an upstream or a first end 125 and a downstream or a second end 127 with respect to a longitudinal axis $L_A$ of the valve support 120 (FIG. 4A). The frame 110 further includes a plurality of support arms extending radially outward from the valve support 120 and generally in an upstream direction from the downstream end 127 of the valve support 120 (e.g., to reach behind native leaflets of the mitral valve and/or engage cardiac tissue in the subannular region within the left ventricle). In particular, the plurality of support arms can include a main support arm 142 and a plurality or multiple supplemental support arms 144 having variable characteristics (e.g., lengths, widths, reflection angles from the valve support 120, shapes, etc.) configured to engage the leaflets and/or annular cardiac tissue in a manner that distributes loads associated with forces exerted on the heart valve prosthesis 100 during the cardiac cycle and in a manner that inhibits migration of the prosthesis 100. In this way, the plurality of support arms provides the benefits of preventing paravalvular leakage between the prosthesis 100 and the native tissue as well as preventing damage to the native tissue.

At least one of the support arms is a main support arm 142 sized and positioned to extend from a perimeter of the valve support 120 such that main support arm 142 is configured and oriented to engage the middle segment A2 of the anterior leaflet AL (FIG. 3B) of the mitral valve MV without substantially obstructing the left ventricular outflow tract (LVOT, FIG. 1). As shown in FIGS. 4A-4D, the heart valve prosthesis 100 further incorporates a plurality of supplemental support arms 144 around a circumference of the valve support 120 of the heart valve prosthesis 100, and in some embodiments, the prosthesis 100 may include the plurality of supplemental support arms 144 in sets or groupings, e.g., first and second sets or groupings so as to engage the anterior and posterior leaflets, respectively. Additionally, the supplemental support arms 144 may extend from the valve support 120 independently of other components including the main support arm 142 and/or other supplemental support arms 144, such as shown in FIGS. 4A, 4B and 4D.

As shown in FIG. 4D, the supplemental support arms 144 of the heart valve prosthesis 100 include a first set of supplemental support arms 146 (individually referred to as 146a, 146b, 146c and 146d) distributed on either side of the main support arm 142 and on an anterior side of the heart valve prosthesis 100 so as to be configured to be aligned with the anterior leaflet AL (FIG. 3B). The supplemental support arms 144 of the heart valve prosthesis 100 further include a second set of supplemental support arms 148 (individually referred to as 148a, 148b and 148c) distributed about or on a posterior side of the heart valve prosthesis 100 so as to be configured to be aligned with the posterior leaflet PL (FIG. 3B). The first and second sets of supplemental support arms 146, 148 are configured to at least partially engage subannular tissue such that the heart valve prosthesis 100 is supported by the annulus AN when the prosthetic valve component 130 is closed during systole. In accordance with embodiments hereof, each of supplemental support arms 146a-146d may be referred to as a tall or taller supplemental support arm and each of supplemental support arms 148a-148c may be referred to as a short or shorter supplemental support arm, with "tall" or "taller" and "short" or "shorter" referring to the length of the supplemental support arms 146a-146d relative to the length of the supplemental support arms 148a-148c. As well it should be understood that when either of the terms supplemental support arm 144 or supplemental support arms 144 is used herein (or in the figures) that the term is intended to refer to a supplemental support arm or supplemental support arms of one or both of the first and second sets of supplemental support arms 146 and 148.

Figure 5:
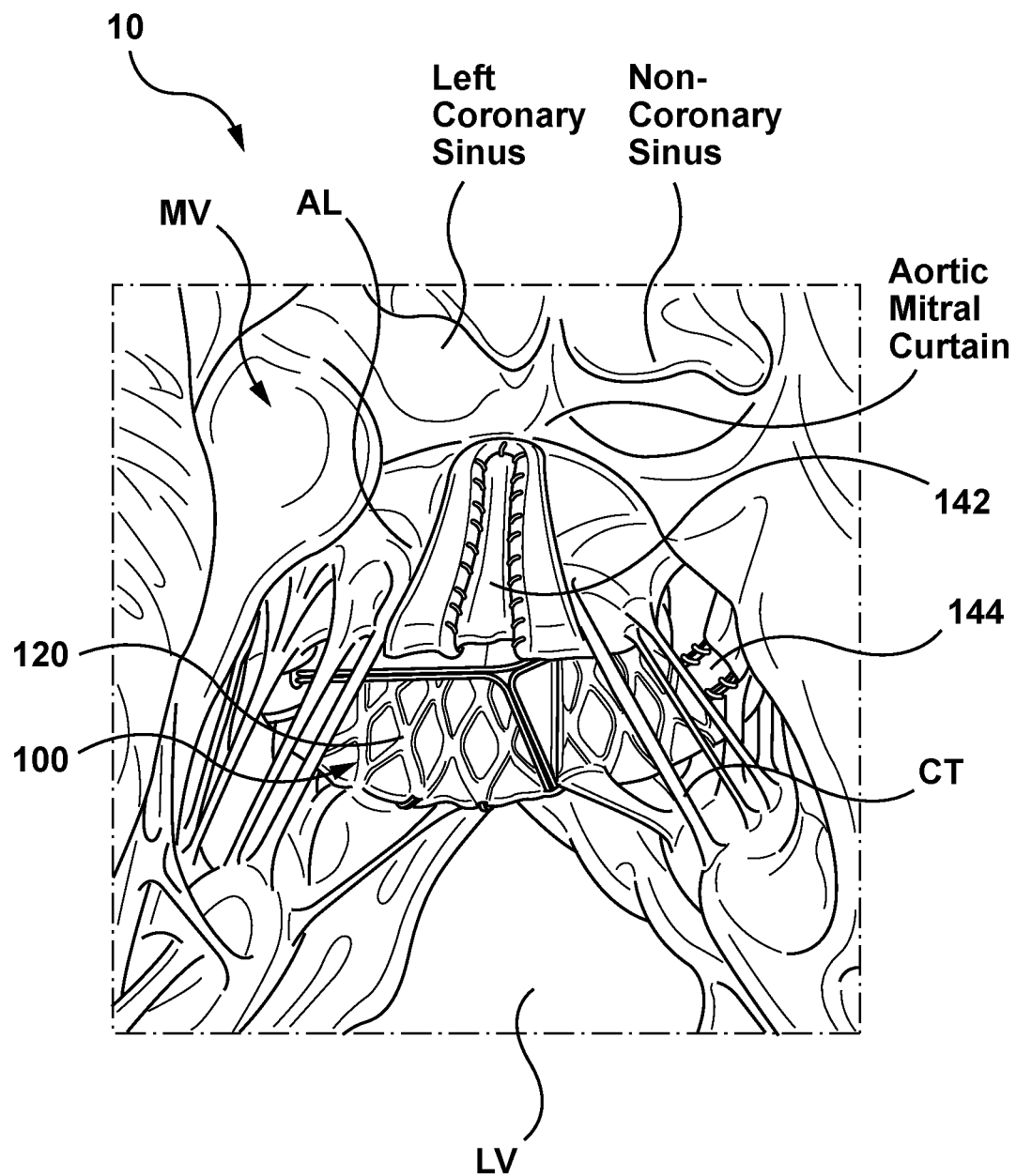
FIG. 5 is a schematic illustration showing a bottom or inferior view of a native mitral valve in the heart viewed from the left ventricle and showing the heart valve prosthesis of FIGS. 4A-4D implanted at the native mitral valve in accordance with an embodiment of the present technology.

FIG. 5 is a schematic illustration showing a bottom or inferior view of a native mitral valve MV in the heart 10 viewed from the left ventricle LV and showing the heart valve prosthesis 100 of FIGS. 4A-4D implanted at the native mitral valve MV in accordance with an embodiment of the present technology. As shown in this illustration, the main support arm 142 is oriented to receive and capture the anterior leaflet AL at the A2 segment proximate to the aortic-mitral curtain and the left and non-coronary cusps (FIG. 3B). The supplemental support arms 144 extend around the anterior leaflet AL and/or posterior leaflet PL (not shown) and between chordae tendinae CT of the mitral valve MV when the prosthesis is implanted. As best seen in FIG. 5, the main support arm 142 on the anterior-oriented side of the prosthesis 100 can be configured to extend through a gap in the chordae tendinae CT near the center of the native anterior leaflet AL, while the supplemental support arms 144 are sized to extend through the chordae tendinae CT, behind the respective leaflets AL, PL and to the annulus.

In some embodiments, and as shown in the radially expanded configuration of FIGS. 4A and 4B, the frame 110 further includes an inflow portion 150, such as radially-extending segment 150 at least partially surrounding and extending from the upstream end 125 of the valve support 120. The radially-extending segment 150 can include a plurality of self-expanding struts 152 configured to radially expand when the heart valve prosthesis 100 is deployed to the expanded configuration. In some arrangements, the radially-extending segment 150 can engage tissue on or above the annulus when implanted within a native mitral valve space. In this embodiment, the radially-extending segment 150 can retain the valve support 120 in a desired position within the native valve region (e.g., between the native leaflets and annulus of the mitral valve). Referring to FIGS. 4A, 4C and 4D, the radially-extending segment 150, the valve support 120 and/or one or more portions of the plurality of support arms 142, 144 can include a sealing material 160 to prevent leakage of blood (e.g., paravalvular leakage) between the implanted heart valve prosthesis 100 and the native heart tissue. For example, the sealing material 160 can extend around an upper or upstream surface 154 or a lower or downstream surface 155 (FIG. 4A) of the radially-extending segment 150, and/or around an interior wall or surface 122 or an exterior wall or surface 123 of the valve support 120 (shown in FIG. 4C).

Referring to FIG. 4C, the radially-extending segment 150 and valve support 120 are shown having generally circular cross-sectional shapes with the radially-extending segment 150 having a cross-sectional dimension $D_1$ that is greater than a cross-sectional dimension $D_2$ of the valve support 120. In some embodiments, the radially-extending segment 150, the valve support 120 or both can have other cross-sectional shapes, such as to accommodate the D-shaped or kidney-shaped mitral valve. For example, the radially-extending segment 150 and/or valve support 120 may expand to an irregular, non-cylindrical, or oval-shaped configuration for accommodating the mitral valve or to correspond to a shape of another valve. Furthermore, the native valves (e.g., mitral, aortic) can be uniquely sized and/or have other unique anatomical shapes and features that vary between patients, and the prosthesis 100 for replacing or repairing such valves can be suitable for adapting to the size, geometry and other anatomical features of such native valves. For example, the radially-extending segment 150 can expand within the native heart valve region while simultaneously being flexible so as to conform to the region engaged by the radially-extending segment 150. In an embodiment, the radially-extending segment 150 may have a saddle shape preset during the manufacturing processing to match the native annulus profile.

FIGS. 4A-4C show the radially-extending segment 150 having the plurality of struts 152 that outwardly extend from the exterior wall 123 at the first end 125 of the valve support 120. In one embodiment, the struts 152 are arranged relatively evenly about a circumference of the valve support 120, and individual struts 152 join an adjacent strut 152 at a crown 156. In one embodiment the crowns 156 have an atraumatic tip 157 that prevents injury to the cardiac tissue during deployment and through the cardiac cycle. Examples of suitable radially-extending segments 150 are described in U.S. Patent Publication No. 2015/0119982, which is incorporated by reference herein in its entirety.

Referring to FIGS. 4C and 4D, the prosthetic valve component 130 may be coupled to the interior wall 122 of the valve support 120 for governing blood flow through the heart valve prosthesis 100. For example, the prosthetic valve component 130 can include a plurality of leaflets 132 (shown individually as 132a-c) that coapt and are configured to allow blood flow through the heart valve prosthesis 100 in a downstream direction (e.g., from the first or upstream end 125 to the second or downstream end 127) and to inhibit blood flow in an upstream or retrograde direction (e.g., from the second end 127 to the first end 125). While the prosthetic valve component 130 is shown having a tricuspid arrangement, it is understood that the prosthetic valve component 130 can have 2 leaflets 132 (bicuspid arrangement, not shown) or more than three leaflets 132 that coapt to close the prosthetic valve component 130. In one embodiment, the leaflets 132 can be formed of bovine pericardium or other natural material (e.g., obtained from heart valves, aortic roots, aortic walls, aortic leaflets, pericardial tissue, such as pericardial patches, bypass grafts, blood vessels, intestinal submucosal tissue, umbilical tissue and the like from humans or animals) that are mounted to the interior wall 122 of the valve support 120. In another embodiment, synthetic materials suitable for use as valve leaflets 132 include DACRON® polyester (commercially available from Invista North America S.A.R.L. of Wilmington, Del.), other cloth materials, nylon blends, polymeric materials, and vacuum deposition nitinol fabricated materials. In yet a further embodiment, valve leaflets 132 can be made of an ultra-high molecular weight polyethylene material commercially available under the trade designation DYNEEMA from Royal DSM of the Netherlands. With certain leaflet materials, it may be desirable to coat one or both sides of the leaflet with a material that will prevent or minimize overgrowth. It can be further desirable that the leaflet material is durable and not subject to stretching, deforming, or fatigue.

Figure 6:
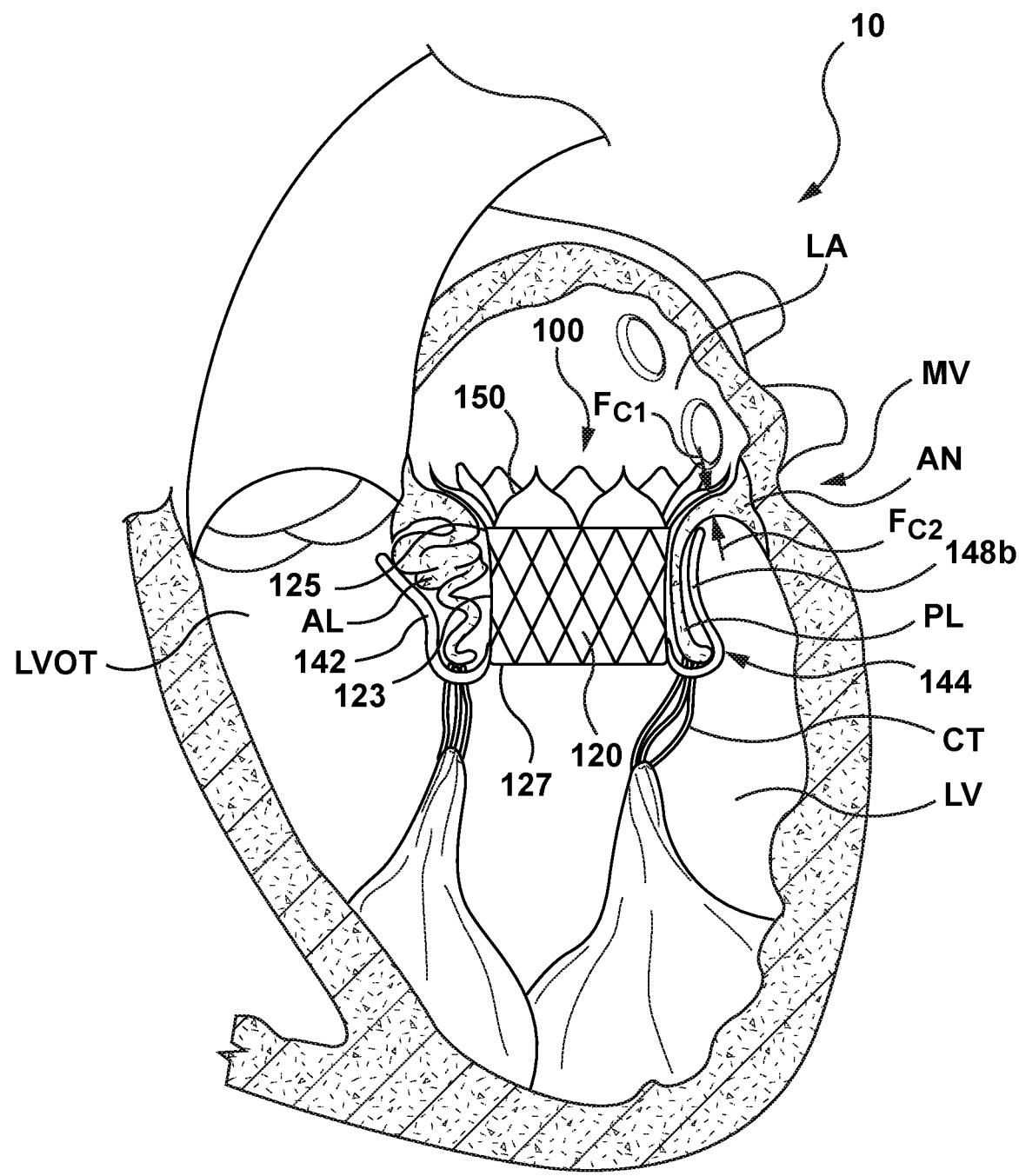
FIG. 6 illustrates a cut-away view of a heart showing a partial side view of a heart valve prosthesis implanted at a native mitral valve in accordance with an embodiment of the present technology.

FIG. 6 illustrates a cut-away view of a heart 10 showing a partial side view of the heart valve prosthesis 100 implanted at a native mitral valve MV in accordance with an embodiment of the present technology. The prosthesis 100 is shown in FIG. 6 having only a main support arm 142 and one diametrically opposed supplemental support arm 148b for purposes of illustration only. Generally, when implanted, the upstream end 125 of the valve support 120 is oriented to receive blood inflow from a first heart chamber, e.g., left atrium LA for mitral valve MV replacement, left ventricle for aortic valve replacement, etc., and the downstream end 127 is oriented to release blood outflow into a second heart chamber or structure, e.g., left ventricle LV for mitral valve MV replacement, aorta for aortic valve replacement.

Referring to FIGS. 4A, 4B, 4D, 5 and 6 together, the plurality of support arms 142, 144 extend from the downstream end 127 of the valve support 120, and are spaced about the circumference of the exterior wall 123 of the valve support 120 (FIG. 4D). As shown in FIG. 4D, the support arms 142, 144 can be grouped closer together and/or farther apart and extend from the valve support 120 at positions that are configured to generally align with the anterior and posterior leaflets of the mitral valve when deployed. For example, the main support arm 142 is configured to be generally aligned with the middle segment or scallop A2 of the anterior leaflet AL (FIGS. 3B and 5). The first set of supplemental support arms 146 flank the main support arm 142 such that they will interact with the anterior leaflet AL at the A1 and A3 segments proximate the commissures. For example, supplemental support arms 146a and 146b of the first set of supplemental support arms 146 are configured to reach behind the anterior leaflet (e.g., interact with the ventricle side or outward-facing surface) near the anterolateral commissure AC, while the remaining supplemental support arms 146c and 146d of the first set of supplemental support arms 146 are configured to reach behind the anterior leaflet (e.g., interact with the ventricle side or outward-facing surface) near the posteromedial commissure PC. Likewise, as shown in FIG. 4D, the second set of supplemental support arms 148a, 148b, 148c are arranged about the remainder of the circumference of the exterior wall 123 of the valve support 120 such that they will interact with the posterior leaflet PL at the P1, P2 and P3 segments, respectively. In this example, the supplemental support arm 148b of the second set of support arms 148 is diametrically opposed to the main support arm 142. In other arrangements, however, another of the second set of supplemental support arms 148 (e.g., 148a or 148c) may be oriented so as to be diametrically opposed with the main support arm 142 and/or configured to interact with the P2 segment of the posterior leaflet PL. In general, including in arrangements not shown, the plurality of support arms can be generally evenly spaced, unevenly spaced, grouped, irregularly spaced, etc. about the circumference.

The embodiment shown in FIG. 4D has eight support arms spaced about the circumference of the valve support 120, including one main support arm 142 and seven supplemental support arms 144. Of the seven supplemental support arms 144, four are in the first set of supplemental support arms 146 configured to extend behind portions of the anterior leaflet and/or near the anterolateral and posteromedial commissures AC, PC. Additionally, three of the supplemental support arms 144 are in the second set of supplemental support arms 148 configured to extend behind portions of the posterior leaflet. In alternative arrangements, the prosthesis 100 can include more or less than 8 support arms and/or other combinations of main support arms 142 and supplemental support arms 144, for example by way of illustration but not limitation, two main support arms, two to six supplemental support arms, greater than seven supplemental support arms, nine supplemental support arms, etc.

Referring to FIGS. 4A, 4B and 6 together, each of the plurality of support arms may extend from the valve support 120 at or near the downstream or second end 127 and may be described as extending generally toward the upstream or first end 125 along or in parallel with the exterior wall 123 of the valve support 120. Stated another way each of the plurality of support arms may be considered to be flared away from valve support 120 to engage native commissures when the prosthesis is implanted in the expanded or deployed state. When the prosthesis is in the expanded or deployed state, as shown in FIG. 4A, the plurality of support arms may be configured to longitudinally extend in an upstream direction to variable heights with respect to a height $H_1$ of the valve support 120. In the embodiment shown in FIG. 4A, a height or deployed height $H_2$ of the deployed or expanded main support arm 142 is less than a height or deployed height $H_3$ of the deployed or expanded plurality of supplemental support arms 144. In other arrangements the height $H_2$ and the height $H_3$ can be substantially the same. In embodiments hereof as described in more detail below, when referring only to the supplemental support arms 144, although lengths are different for the first and second sets of supplemental support arms 146 and 148 when in the crimped, straightened or delivery configuration, their heights, once in the deployed configuration are configured to be the same. In embodiments hereof the deployed heights are substantially the same because the longer arms (arms 146a-146d) are set out at a wider angle, and therefore have less total height when deployed, as compared to the shorter arms (arms 148a-148c), which in an embodiment may deploy nearly parallel to the valve housing, creating similar heights between the sets. An objective of having all the supplemental arms (the longer and shorter ones) with the same height once deployed is that each will then contact the ventricular side of the annulus, which is more or less planar. In embodiments hereof, the heights $H_2$, $H_3$ are measured relative to the second end 127 of the valve support 120. The height $H_2$ achieved by the main support arm 142 (e.g., whether less than or equal to the height $H_3$ of the supplemental support arms 144) is configured to prohibit the main support arm 142 from impinging upon the leaflets of the aortic valve AV (FIGS. 3B and 6). By avoiding the cardiac tissue along the mid-anterior portion of the mitral valve MV annulus AN, the main support arm 142 can capture the anterior leaflet tissue without substantially occluding the LVOT from within the left ventricle LV (FIG. 6).

In general, the first and second sets of supplemental support arms 146 and 148 are configured to extend to substantially or essentially the deployed height $H_3$ relative to the second end 127 of the valve support 120 and each supplemental support arm terminates in a rounded, curved, or otherwise atraumatic tip or end portion 145. In an embodiment, the deployed height $H_3$ disposes or positions each end portion 145 of the supplemental support arms of the first and second sets of supplemental support arms 146, 148 at substantially the same longitudinal position relative to the longitudinal axis $L_A$ of the valve support 120. The end portions 145 are configured to atraumatically engage tissue at or near the subannular tissue so as to inhibit tissue damage due to penetration, tissue erosion and/or to resist movement of the heart valve prosthesis 100 in an upstream direction during ventricular systole, as is described further herein. In the embodiment shown in FIGS. 4A and 4B, the height $H_3$ of the first and second sets of supplemental support arms 146, 148 is also configured to allow the supplemental support arms to extend around and behind the respective leaflets AL, PL to engage the fibrous connective tissue of the subannular surface and/or proximate muscular tissue associated with a wall of the left ventricle LV (see, e.g., supplemental support arm 148b in FIG. 6). The deployed height $H_3$ of the first and second sets of supplemental support arms 146, 148 is sufficient to allow the respective end portions 145 to contact and act against (e.g., in opposition to) the radially-extending segment 150 when in an expanded state. When positioned for use within a native mitral valve MV, the heart valve prosthesis 100 is configured to be deployed in a manner that captures and subsequently pinches annular tissue between the radially-extending segment 150 and the end portions 145 of the supplemental support arms 144 (FIG. 6). In another embodiment, when in an expanded state an apex or apices 153 (e.g., lower surface) of struts of the radially-extending segment 150 can be longitudinally separated from the end portions 145 of the supplemental support arms 144 by a gap (not shown). When implanted, the gap can be sized to receive annular tissue therein.

In one embodiment, an apex or apices 153 of the struts 152 of inflow portion 150 oppose a respective upstream oriented end portion 145 of a respective supplemental support arm 144 in such a manner that provides compressive forces $Fc_1$ and $F_{C2}$, which act upon the contacted tissue of the annulus therebetween when implanted (FIG. 4A). Accordingly, the compressive forces $Fc_1$ and $Fc_2$ may be aligned and/or opposed to each other such that annular tissue is captured between the radially-extending segment 150 and the supplemental support arms 144 (first and second sets of supplemental support arms 146, 148) distributed about the perimeter of the valve support 120 (FIG. 6). In some instances, a respective apex 153 and a corresponding or opposing end portion 145 meet (e.g., when struts 152 are circumferentially- and radially-aligned with the end portion 145 of the supplemental support arms 144 such that the compressive forces $Fc_1$ and $F_{C2}$ are directly opposed to effectively pinch the annulus AN therebetween) or otherwise overlap (e.g., when struts 152 are off-set from the end portion 145 as shown in FIGS. 4A and 4B) when the prosthesis 100 is full expanded (e.g., unbiased) and no gap is provided. In such embodiments, annular tissue can be captured between the end portions 145 of the supplemental support arms 144 and the lower surface of the radially-extending segment 150 in a manner that places bias on or deflects at least one of the supplemental support arms 144 (e.g., in a downstream direction) and/or one or more struts 152 of the radially-extending segment 150 (e.g., in an upstream direction). In arrangements providing a gap or in the arrangements hereof where no gap is provided, load distribution between the plurality of support arms 142, 144 disposed about the circumference can inhibit migration of the heart valve prosthesis 100 over time, minimize load on native leaflet tissue and/or chordae tendinae CT (e.g., to prevent damage due to stretching and/or deformation over time), and/or provide a gasket-like sealing effect about the circumference of the prosthesis 100 against the annular tissue of the native mitral valve MV. In accordance therewith, the supplemental support arms 144 are splayed circumferentially so that end portions 145 are spaced apart along the native annulus so as to distribute the load across a wider area of the native subannular surface.

Figure 7:
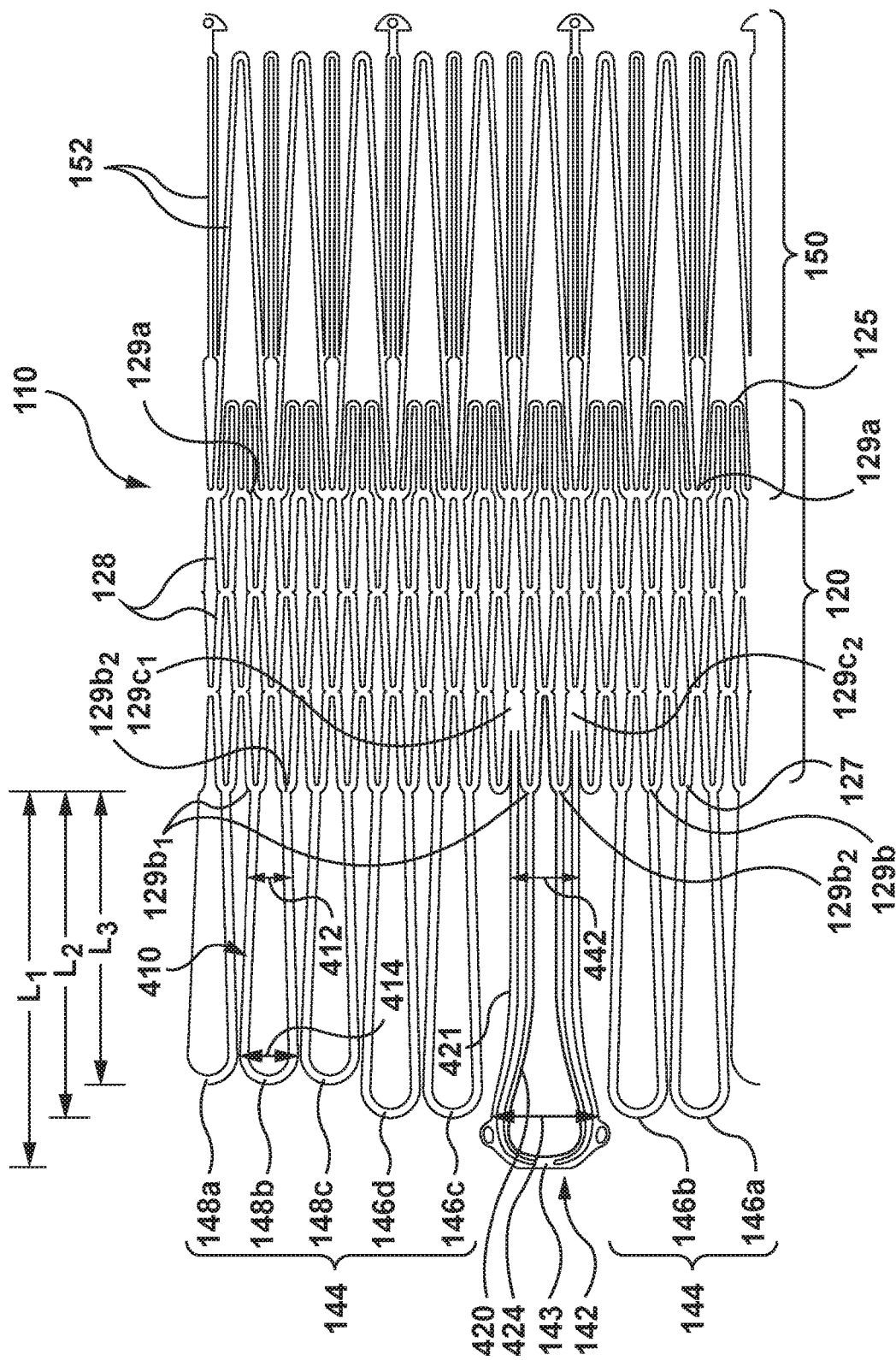
FIG. 7 shows a cut pattern for a frame of the heart valve prosthesis of FIG. 4A in accordance with an embodiment of the present technology.

In some embodiments described herein, and in order to transform or self-expand between an initial compressed configuration (e.g., in a delivery state, not shown) and the deployed configuration (FIGS. 4A-6), the frame 110 is formed from a resilient or shape memory material, such as a nickel titanium alloy (e.g., nitinol), that has a mechanical memory to return to the deployed or expanded configuration. In one embodiment, the frame 110 can be a unitary structure that defines the radially-extending segment 150 at the inflow portion of the prosthesis 100, the valve support 120 and the plurality of support arms 142, 144, and the frame 110 so described may be made from stainless steel, a pseudo-elastic metal such as nickel titanium alloy or nitinol, or a so-called super alloy, which may have a base metal of nickel, cobalt, chromium, or other metal. In one embodiment, and as shown in FIG. 7, the frame 110 can be formed as a unitary structure, for e.g., from a laser cut, fenestrated, nitinol or other metal tube. Mechanical memory may be imparted to the structure that forms the frame 110 by thermal treatment to achieve a spring temper in the stainless steel, for example, or to set a shape memory in a susceptible metal alloy, such as nitinol. The frame 110 may also include polymers or combinations of metals, polymers or other materials. In one embodiment, the valve support 120 can be a balloon-expandable tubular metal stent, and the radially-extending segment 150 and the support arms 142, 144 of the frame 110 may be formed from material and by methods so as to be self-expanding as described above.

FIG. 7 shows a cut pattern for a frame 110 of the heart valve prosthesis 100 of FIG. 4A in accordance with an embodiment of the present technology. As illustrated in FIG. 7, the frame 110 can include a unitary cut structure that includes the valve support 120, the radially-extending segment 150 generally extending from the first end 125 of the valve support 120, and the plurality of support arms 142, 144 extending from the second end 127 of the valve support 120. In other embodiments, the frame 110 can include separately manufactured components that are coupled, linked, welded, or otherwise mechanically attached to one another to form the frame 110.

Referring to FIGS. 4B and 7 together, the frame 110 can be a flexible metal frame or support structure having a plurality of ribs and/or struts (e.g., struts 128, 152) geometrically arranged to provide a latticework capable of being radially compressed (e.g., in a delivery state, not shown) for delivery to a target native valve site, and capable of radially expanding (e.g., to the radially expanded configuration shown in FIGS. 4A and 4B) for deployment and implantation at the target native valve site (FIGS. 5 and 6). Referring to the valve support 120 shown in FIGS. 4A and 4B, the ribs and struts 128 can be arranged in a plurality of geometrical patterns that can expand or flex and contract while providing sufficient resilience and strength for maintaining the integrity of the prosthetic valve component 130 housed within. For example, the struts 128 can be arranged in a circumferential pattern about the longitudinal axis LA, wherein the circumferential pattern includes a series of diamond, zig-zagged, sinusoidal, or other geometric shapes.

The radially-extending segment 150 can be coupled to or extend from the upstream portion 124 of the valve support 120 (e.g., at attachment points 129a between the struts 128 as defined by a diamond-shaped geometry of the valve support 120). Likewise, the plurality of support arms 142, 144 can be coupled to or extend from the downstream portion 126 of the valve support 120 (e.g., at attachment points 129b on endmost peaks or crowns between adjacent struts 128 of the valve support 120; FIGS. 4B and 7). Other arrangements and attachment points are contemplated for coupling one or more of the main support arm 142 and/or supplemental support arms 144 as well as the radially-extending segment 150 to the valve support 120. In particular embodiments, and as shown in FIGS. 4B and 7, each supplemental support arm 144, such as supplemental support arm 148b, can comprise an arm segment 410 of the frame 110 coupled to the valve support 120 at a first attachment point 129b1 and a second attachment point 129b2 wherein the arm segment 410 defines a loop therebetween. In one embodiment, the arm segment 410 can be integral with the frame 110 such that the arm segment 410 is cut or formed from a common sheet or tube as the one or more struts 128. In another embodiment, the arm segment 410 and valve support 120 may be coupled by a variety of methods known in the art, e.g., soldering, welding, bonding, rivets or other fasteners, mechanical interlocking, or any combination thereof.

In a similar manner, the main support arm 142 can comprise inner and outer arm segments 420, 421 configured to provide together additional resiliency to the main support arm 142 so as to engage and trap leaflet tissue between the main support arm 142 and the exterior surface 123 of the valve support 120 (FIGS. 4B and 7). As shown in FIGS. 4B and 7, the inner arm segment 420 can be coupled to endmost peaks or crowns of the valve support 120 at first and second attachment points $129b_1$, $129b_2$ in a similar manner as the arm segments 410 of the supplemental support arms 144, thereby forming a loop therebetween. The outer arm segment 421 can be coupled to attachment points $129c_1$ and $129c_2$ between the struts 128 as defined by the diamond-shaped geometry of the valve support 120, and form a loop therebetween that generally follows the shape of the inner arm segment 420. In some embodiments, the inner and outer arm segments 420, 421 may be connected (e.g., bonded, welded or otherwise attached to one another) at any point along the length of the inner and outer arm segments 420, 421, and for example, at the tip portion 143 (as shown in FIGS. 4B and 7).

As shown in FIG. 4B, the attachment points $129c_1$ and $129c_2$ are set further apart than attachment point $129b_1$ and $129b_2$, thereby giving the main support arm 142 at least a wider overall base portion 442 than base portions 412 of the supplemental support arms 144. Both base portion 412 and an upper portion 414 of the supplemental support arms 144 have a maximum width $W_1$ configured to fit between and/or minimally interact with chordae tendinae CT during deployment. As best seen in FIG. 4B, the maximum width $W_1$ of each one of the supplemental support arms 144 is less than a width $W_2$ of the base portion 442 or width $W_3$ of an upper portion 424 of the main support arm 142. Accordingly, the main support arm 142 is configured to function as a leaflet capture arm and is sized and proportioned to capture and retain the larger A2 segment or scallop of the anterior leaflet AL, while the supplemental support arms 144 are configured to reach behind the anterior and posterior leaflets AL, PL to contact and engage the dense connective tissue in the subannular region while minimally interacting with the chordae tendinae CT during deployment.

Referring back to FIG. 7, the plurality of support arms 142, 144 are provided with variable lengths. For example, the main support arm 142 is provided with a first length $L_1$, the first set of supplemental support arms 146a-d is provided with a second length $L_2$ less than the first length $L_1$, and the second set of supplemental support arms 148a-c is provided with a third length $L_3$ less than both the first and second lengths $L_1$, $L_2$. In alternative arrangements, groupings of support arms 142, 146, 148 can be provided with lengths greater or less than the lengths of other support arms. The variable lengths $L_1$, $L_2$ and $L_3$ can be provided to accommodate the overall distances (e.g., desired heights $H_2$ and $H_3$) the respective support arms 142, 146, 148 must extend to interact with intended target cardiac tissue when deployed at the native mitral valve. Furthermore, the lengths $L_1$, $L_2$ and $L_3$ can vary with respect to each other and be selected based on the anatomy of the target tissue.

Figure 8A:
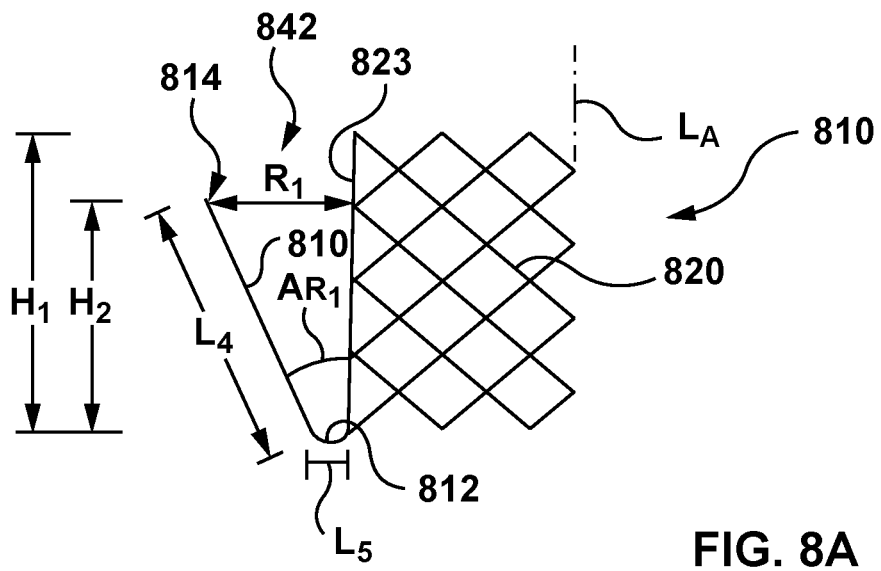
FIGS. 8A-8C are enlarged partial side views of a heart valve prosthesis having a main (FIG. 8A) or various supplemental (FIGS. 8B and 8C) support arms coupled to and extending from a valve support at various angles with respect to a longitudinal axis of the valve support in accordance with further embodiments of the present technology.
Figure 8B:
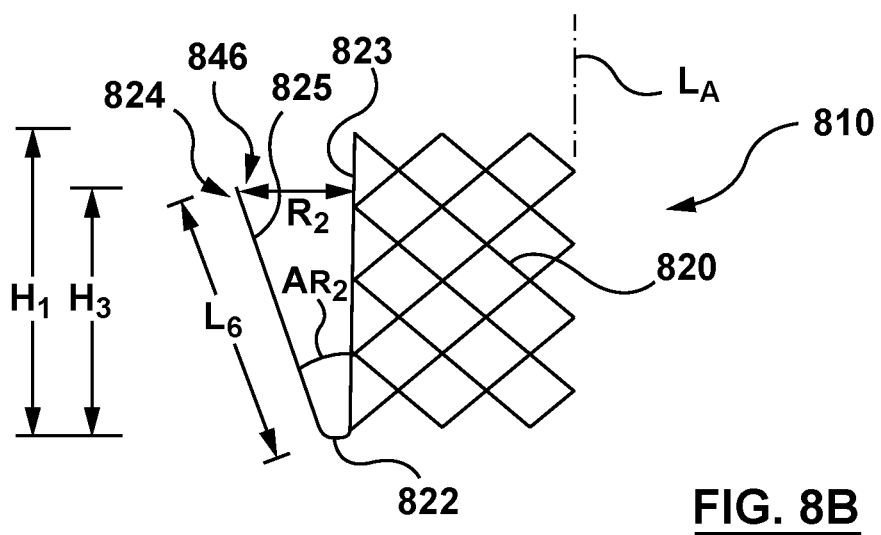
Figure 8C:
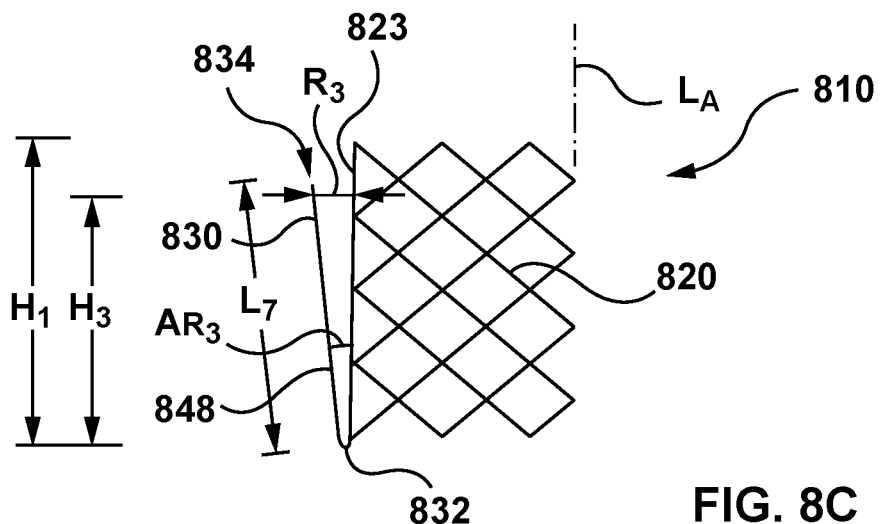

FIGS. 8A-8C are enlarged partial side views of a frame 810 for a heart valve prosthesis in accordance with another embodiment having a main support arm 842 (FIG. 8A) and various supplemental (FIGS. 8B and 8C) support arms 846, 848 coupled to and extending from a valve support 820 at various reflection angles with respect to the longitudinal axis $L_A$ of the valve support 820 in accordance with further embodiments of the present technology. As shown in FIG. 8A, a main support arm 842 comprises an arm body 810 radially off-set from the valve support 120 by a curved region 812 and terminating in a curved atraumatic main arm tip or end portion 814. The arm body 810 has an arm body length $L_4$ and is integral with the curved region 812 that extends the main support arm 842 radially outward from the valve support 820 and in an upstream direction. A first reflection angle $A_{R1}$ or taper angle is formed between the external wall 823 of the valve support 820 and the arm body 810; the first reflection angle $A_{R1}$ is selected such that the main support arm 842 is positionable so that the arm body 810 can sufficiently engage the outward-facing anterior leaflet tissue and wherein the main arm tip 814 does not interact with the aortic leaflets or ventricular wall behind the native anterior leaflet AL. In one embodiment, the first reflection angle $A_{R1}$ may be approximately −10° to approximately 45°, wherein 0 degrees represents a vertical disposition of the main support arm 842 and wherein a negative angle is in a direction toward the valve support 820 and a positive angle is in a direction away from the valve support 820. In other embodiments, the first reflection angle $A_{R1}$ may be from an angle where the tip 814 of the main support arm 842 meets the valve support 820, or conversely may be as great as 90° with respect to the longitudinal axis $L_A$.

With reference to FIG. 8A, the arm body 810 extends from the curved region 812, which is located at a proximal end of the main support arm 842. The curved region 812 can have an extension length $L_5$ which can be selected or optimized for extending the arm body 810 of the main support arm 842 radially outward from the exterior wall 823 of the valve support 820 at a sufficient distance to accommodate the anterior leaflet tissue therebetween. The length $L_4$ of the arm body 810 and the length $L_5$ of the curved region 812 together make up a total or cut length $L_1$ of the main support arm 842, as similarly shown in FIG. 7 for main support arm 142. As illustrated, the valve support 820 is oriented along a central longitudinal axis $L_A$, and the main support arm 842 can also be described as flaring outward relative to the longitudinal axis $L_A$ by the reflection angle $A_{R1}$. In embodiments where the main support arm 842 generally curves outward from the curved region 812 to the arm tip 814 (rather than linear), the reflection angle $A_{R1}$ can continuously change along the length $L_4$ of the arm body 810 (see, e.g., FIG. 4A). In the embodiment shown in FIG. 8A, the reflection angle $A_{R1}$ is consistent along the length $L_4$ of the arm body 810.

In the expanded state shown in FIG. 8A, the main support arm 842 has a main arm height $H_2$ extending from the curved region 812 to the distalmost point of the main support arm 142, which could be the arm tip 814 (shown in FIG. 8A) along an axis parallel to the longitudinal axis $L_A$ of the valve support 820. As discussed above, the main arm height $H_2$ of the main support arm 842 in the expanded state can be selected or optimized such that the arm tip 814 engages a desired location in the subannular anatomy when the prosthesis is in a desired longitudinal position relative to the native mitral valve (e.g., when the supplemental support arms are in engagement with the subannular tissue, and when the radially-extending segment is in engagement with the supra-annular tissue, etc.). In the expanded state, the main arm height $H_2$ is a function of the cut length $L_1$ of the main support arm 842, the length $L_4$ of the arm body 810 and the first reflection angle $A_{R1}$ and can be selected such that main arm height $H_2$ is sufficiently less than the overall height $H_1$ of the valve support 820 and to prevent undesirable interrogation of subannular tissue behind the A2 segment of the anterior leaflet AL.

FIGS. 8B and 8C show first and second supplemental support arm 846, 848 configurations in accordance with another embodiment. FIG. 8B is a partial side view of a heart valve prosthesis showing a supplemental support arm 846 from a first set of supplemental support arms coupled to the valve support 820 and/or extending therefrom. The supplemental support arm 846 may comprise a supplemental support arm body 825 off-set from the valve support 820 by a curved region 822 and terminating in a supplemental support arm tip or end portion 824. The supplemental arm body 825 has an arm body length $L_6$ and is integral with the curved region 822 that extends the first supplemental support arm 846 radially outward from the valve support 820 and in an upstream direction. A second reflection angle $A_{R2}$ is formed between the external wall 823 of the valve support 820 and the supplemental support arm body 825. As illustrated, the first set of supplemental support arms 846 can also be described as flaring outward relative to the longitudinal axis $L_A$ of the valve support 820 by the reflection angle $A_{R2}$. In this embodiment, both the second reflection angle $A_{R2}$ and the supplemental support arm body length $L_6$ are selected such that in the expanded state the arm tips 824 of the first set of supplemental support arms 846 are positionable to engage at least the subannular tissue or ventricular wall behind the native anterior leaflet AL at the A1 or A3 segments (e.g., proximate the anterolateral and posteromedial commissures AC, PC).

A partial side view of a heart valve prosthesis showing a supplemental support arm 848 of a second set of supplemental support arms coupled to the valve support 820 and/or extending therefrom is shown in FIG. 8C. Similar to the supplemental support arm 846, the supplemental support arm 848 comprises a supplemental support arm body 830 off-set from the valve support 120 by a curved region 832 and terminating in a second supplemental support arm tip or end portion 834. The supplemental support arm body 830 has an arm body length $L_7$ and is integral with the curved region 832 that extends the supplemental support arm 848 radially outward from the valve support 820 and in an upstream direction. A third reflection angle $A_{R3}$ is formed between the external wall 823 of the valve support 820 and the supplemental support arm body 830. As illustrated, the second set of supplemental support arms 848 can also be described as flaring outward relative to the longitudinal axis $L_4$ of the valve support 820 by the reflection angle $A_{R3}$. In this embodiment, both the third reflection angle $A_{R3}$ and the supplemental support arm body length $L_7$ are selected such that in the expanded state the arm tips 834 of the second set of supplemental support arms 848 are positionable to engage at least the subannular tissue or ventricular wall behind the native posterior leaflet PL at the P1, P2 or P3 segments.

With reference to FIGS. 8B and 8C together, in the expanded state each of the first set of supplemental support arms 846 and each of the second set of supplemental support arms 848 have substantially or essentially the same or equal supplemental support arm height $H_3$, as measured from the curved regions 822, 832, respectively, to the distalmost points thereof (e.g., the arm tips 824, 834, respectively) along an axis parallel to the longitudinal axis $L_4$ of the valve support 820 (shown in FIGS. 8B and 8C). As discussed above with respect to FIG. 4A, the supplemental arm height $H_3$ can be selected or optimized such that when the prosthesis is deployed the first and second supplemental support arm tips 824, 834 each engage the annulus AN in a manner that provides a compressive force opposite the radially-extending segment 150 deployed above the annulus AN to pinch the annular tissue therebetween.

The supplemental support arm height $H_3$ of each of the first set of supplemental support arms 846 shown in FIG. 8B is a function of a total or cut length $L_2$ of the first set of supplemental support arms 846, as similarly shown in FIG. 7 for supplemental support arm 146, the length $L_6$ of the arm body 820 and the second reflection angle $A_{R2}$ and can be selected such that deployed height $H_3$ is less than the overall deployed height $H_1$ of the valve support 820 (FIG. 8B). Likewise, the supplemental support arm height $H_3$ of each of the second set of supplemental support arms 848 shown in FIG. 8C is a function of a total or cut length $L_3$ of the second set of supplemental support arms 848, as similarly shown in FIG. 7 for supplemental support arm 148, the length $L_7$ of the arm body 830 and the third reflection angle $A_{R3}$. Referring to FIGS. 8B and 8C together, while the first set of supplemental support arms 846 have an overall or cut length $L_2$ that is greater than the overall or cut length $L_3$ of the second set of supplemental support arms 848, and have the arm body length $L_6$ that is greater than the arm body length $L_7$ of the second set of supplemental support arms 848, both the first and second sets of supplemental support arms 846, 848 have the same deployed height $H_3$ in an expanded or natural state because the second reflection angle $A_{R2}$ of the first set of supplemental support arms 846 is greater than the third reflection angle $A_{R3}$ of the second set of supplemental support arms 848. In embodiments hereof, the second reflection angle $A_{R2}$ and/or the third reflection angle $A_{R3}$ may be approximately 0° to approximately 45°, wherein 0 degrees represents a vertical disposition of the respective supplemental support arm and wherein a positive angle is in a direction away from the valve support 820. In other embodiments, the second reflection angle $A_{R2}$ and/or the third reflection angle $A_{R3}$ may be such that a tip 824, 834 of the respective supplemental support arm 846, 848 touches the valve support 820, or conversely may be as great as 90° with respect to the longitudinal axis $L_4$. In each of the foregoing embodiments, the second reflection angle $A_{R2}$ of the longer supplemental support arm 846 is greater than the third reflection angle $A_{R3}$ of the shorter supplemental support arm 848. Other reflection angles are contemplated and one of ordinary skill in the art will recognize that supplemental support arms 144, 146, 148, 846, 848 can have independently variable reflection angles whether such arms are within a particular set of supplemental support arms or separately configured.

In the expanded or deployed state of the prosthesis, with reference to FIGS. 8A-8C, end portions or tips 814, 824, 834 of supports arms 842, 846, 848, respectively, have different radial positions relative to the valve support 820 due to their respective arm lengths $L_4$, $L_6$, $L_7$ and reflection angles $A_{R1}$, $A_{R2}$, $A_{R3}$. In particular, end portion 814 of the main support arm 842 is a radial distance $R_1$ from the external wall 823 of valve support 820, each end portion 824 of the first set of supplemental support arms 846 is substantially or essentially a radial distance $R_2$ from the external wall 823 of valve support 820, and each end portion 834 of the second set of supplemental support arms 848 is substantially or essentially a radial distance $R_3$ from the external wall 823 of valve support 820. In embodiments in accordance herewith, radial distances $R_1$, $R_2$, and $R_3$ may be selected so that each of the support arms 842, 846, 848 interacts with a desired, respective portion of the native heart anatomy when deployed, as described herein. In embodiments in accordance herewith, radial distance $R_1$ may be greater than each of radial distances $R_2$, $R_3$. In embodiments in accordance herewith, the radial distance $R_2$ may be greater than the radial distance $R_3$.

Referring to FIGS. 3B, 4D and 8A-8C together, the heart valve prosthesis 100 is configured with a plurality of support arms having the variable characteristics (e.g., length, arm body length and reflection angle) to provide subannular engagement consistently about the D-shaped profile of the mitral valve annulus AN. For example, the further extending (e.g., longer) first set of supplemental support arms 146, 846 provide annular engagement across the major axis of the D-shaped profile spanning from the anterolateral commissure AC to the posteromedial commissure PC. Likewise, the second set of supplemental support arms 148, 848 are shorter and contact the subannular tissue behind the posterior leaflet PL and in a more proximal position to the valve support 120, 820 (e.g., have a smaller reflection angle), thereby providing load bearing distribution around the outer curved portion of the D-shaped profile of the annulus AN (see, e.g., FIGS. 3B and 4D). Advantageously, while providing more evenly distributed load bearing about the D-shaped annulus AN, the first and second supplemental support arms 146, 846, 148, 848 have a narrower profile that permits minimal interaction or disturbance of the chordae tendinae CT during and after deployment.

Referring to FIGS. 4A-6 together, several features of the prosthesis 100 provide resistance to movement of the prosthesis 100, promote tissue ingrowth, minimize or prevent paravalvular leakage and/or minimize native tissue erosion when implanted in the radially expanded configuration. For example, the radially-extending segment 150 can be positioned to expand within the atrial space above the mitral valve and engage cardiac tissue within the atrial space. In particular, at least the lower surface or apex 153 of the arching or S-shaped struts 152 that from the radially-extending segment 150 can provide a tissue engaging region for contacting the supra-annular tissue, for example to provide sealing against paravalvular leakage and to inhibit downstream migration of the prosthesis 100 relative to the native annulus (FIG. 4A).

In some embodiments, upwardly oriented portions 158 of struts 152, each of which rises to join at a respective crown 156 an adjacent upwardly oriented portion 158 of an adjoining or adjacent strut 152, can provide further tissue contact zones that can further inhibit downstream movement of the prosthesis 100 relative to the native annulus, and inhibit rocking or side-to-side rotation of the prosthesis 100 within the native valve during the cardiac cycle, thereby inhibiting paravalvular leakage and assuring alignment of the prosthetic valve component 130 within the native annulus (FIGS. 4A and 6). In other embodiments, the radially-extending segment 150 can be a flange, a brim, a ring, finger-like projections or other projection into the atrial space for at least partially engaging tissue at or above a supra-annular region thereof.

Referring to FIGS. 4A, 4B and 4D, 5 and 6 together, the plurality of support arms 142, 144 are configured to engage both the native leaflets (if present) and/or the subannular region of the mitral valve MV within the ventricular space. In one embodiment, at least the main support arm 142 is configured to engage an outside surface (e.g., ventricle-facing side) of the anterior leaflet AL such that the leaflet is captured between the main support arm 142 and the exterior wall 123 of the valve support 120. In one such embodiment, the main support arm 142 can be biased toward the exterior wall 123 of the valve support 120 such that a compressive force presses the anterior leaflet AL against the exterior wall 123 in a manner that pinches, grasps, crimps or otherwise confines the leaflet between the main support arm 142 and the exterior wall 123 of the valve support 120 (FIG. 6). To further inhibit upstream migration of the prosthesis 100 with respect to the native valve annulus AN, the first and second sets of supplemental support arms 146, 148 are configured to engage the subannular region (e.g., behind the anterior and posterior leaflets AL, PL, respectively) via the atraumatic tip portions 145.

In some embodiments, portions of the prosthesis 100, such as upstream, downstream and/or interior surfaces of the radially-extending segment 150 and the valve support 120, and/or upstream and/or downstream surfaces of each of the plurality of support arms, can be fully or at least partially covered by a sealing material 160 (FIG. 4A). In the embodiment shown in FIG. 4A, the sealing material 160 extends around at least the downstream surface 155 of the radially-extending segment 150, around the interior wall 122 of the valve support 120, and around at least portions of each of the plurality of support arms.

In another embodiment as best shown in FIG. 4D, a tent-like cushioning strip 160a of a sealing material 160, or of another material (like foam, soft fabric, velour), may extend across and between curved regions 422, 432 (see e.g., curved regions 822, 832 of supplemental support arms 846, 848 in FIGS. 8B and 8C) of the supplemental support arms 146a-d and 148a-c to thereby providing a tent-like structure spanning the plurality of supplemental support arms. The tent-like cushioning strip 160a spanning across and between the curved regions 422, 432 of the plurality of supplemental support arms 146a-d, 148a-c may prevent damage to the chordae tendinae CT and/or prevent the chordae tendinae CT from interacting with metal portions of the supplemental support arms and the valve support 120. As shown in FIG. 4D, the cushioning strip 160a extends across upstream surfaces of the curved regions 422, 432 of the plurality of supplemental support arms 146a-d, 148a-c.

The sealing material 160 can prevent paravalvular leakage as well as provide a medium for tissue ingrowth following implantation, which can further provide biomechanical retention of the prosthesis 100 in the desired deployment location within the native heart valve region. In some embodiments, the sealing material 160, the cushioning strip 160a, or portions thereof may be a low-porosity woven fabric, such as polyester, DACRON® polyester, or polytetrafluoroethylene (PTFE), which creates a one-way fluid passage when attached to the frame 110. In one embodiment, the sealing material 160, the cushioning strip 160a, or portions thereof may be a looser knit or woven fabric, such as a polyester or PTFE knit, which can be utilized when it is desired to provide a medium for tissue ingrowth and the ability for the fabric to stretch to conform to a curved surface. In another embodiment, polyester velour fabrics may alternatively be used for at least portions of the sealing material 160, the cushioning strip 160a, or portions thereof such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example. In another embodiment, the sealing material 160 or portions thereof may be a natural graft material, such as pericardium or another membranous tissue.

Selected Systems and Methods for Delivery and Implantation of Prosthetic Heart Valve Devices Several suitable delivery and deployment methods are discussed herein and further below; however, one of ordinary skill in the art will recognize a plurality of methods suitable to deliver the prosthesis 100 to the targeted native valve region (e.g., percutaneous, transcatheter delivery using antegrade approaches or retrograde approaches). Additionally, one of ordinary skill in the art will recognize a plurality of methods suitable to deploy the prosthesis 100 from a compressed configuration for delivery to the expanded configuration illustrated in FIG. 4A.

Figure 9:
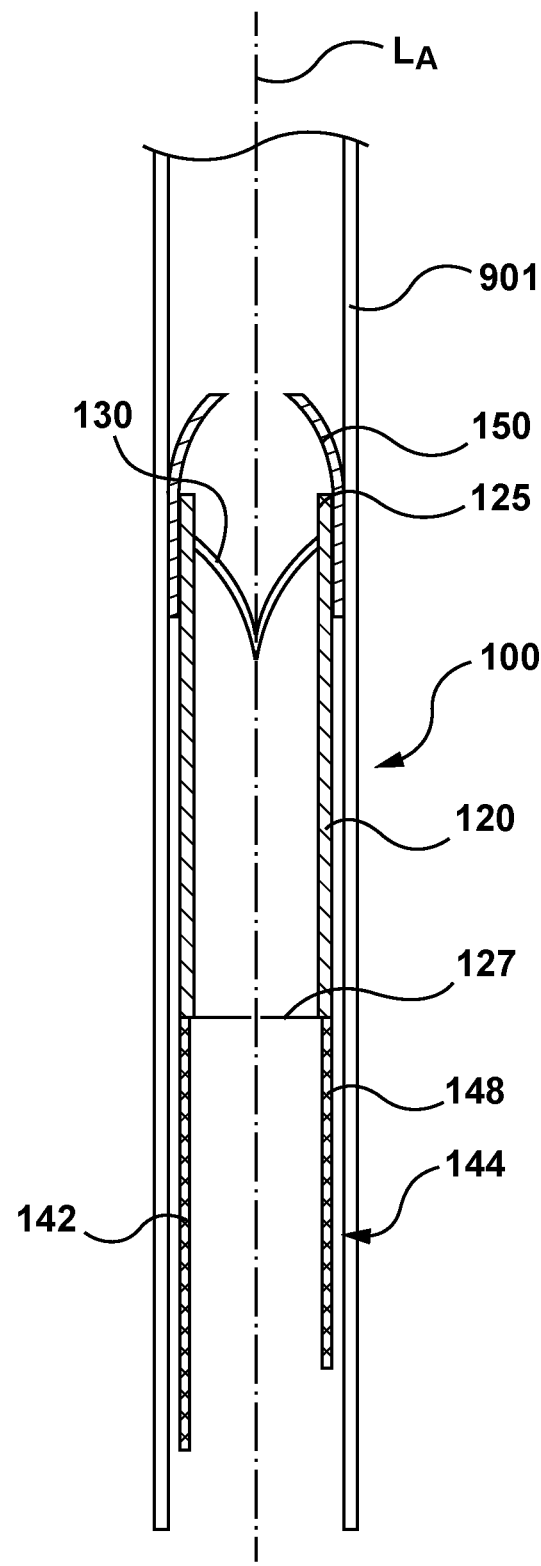
FIG. 9 is an enlarged sectional view of the heart valve prosthesis of FIGS. 4A-4D shown in a delivery configuration (e.g., low-profile or radially compressed state) in accordance with an embodiment of the present technology.

FIG. 9 is an enlarged sectional view of the heart valve prosthesis 100 of FIGS. 4A-4D shown in a compressed delivery configuration (e.g., a low-profile or radially compressed state) and in accordance with an embodiment of the present technology. In operation, the heart valve prosthesis 100 can be intravascularly delivered to a desired native valve region of the heart 10, such as near the mitral valve MV, while in the radially compressed configuration and within a delivery catheter (not shown). As shown in FIG. 9, the prosthesis 100 can be configured for delivery within a delivery catheter sheath 901 in the radially compressed state. More particularly, in the radially compressed state, the radially-extending segment 150 can be elongated, folded or otherwise arranged to longitudinally extend in a substantially straightened state from the inflow end 125 of the valve support 120, while the plurality of support arms 142, 144 can be elongated, folded or otherwise arranged to longitudinally extended in a substantially straightened state from the outflow end 127 of the valve support 120 for percutaneous delivery to the targeted native heart valve. Referring to FIG. 9, the plurality of support arms 142, 148 can extend from or beyond the second end 127 of the valve support 120 such that the curved regions thereof (for example 812, 822, 824 (FIGS. 8A-8C)) are generally linear and substantially parallel with the longitudinal axis $L_A$. Upon release of the radial constraint provided by the sheath 901, the radially-extending segment 150 can self-expand to its radially expanded configuration (FIGS. 4A and 4B) while the plurality of support arms 142, 144 can return to their curved state (FIGS. 4A and 4B) as the delivery catheter sheath 901 is withdrawn from covering each). Additionally, in the event that the heart valve prosthesis 100 needs to be repositioned, removed and/or replaced after implantation, the radially-extending segment 150 and the valve support 120 can transition from the radially expanded configuration (e.g., the deployed state) (FIG. 4A) back to the radially contracted configuration (FIG. 9) using a catheter device or other lateral retaining sheath.

Access to the mitral valve or other atrioventricular valve can be accomplished through a patient's vasculature in a percutaneous manner. In a particular embodiment, the approach to the mitral valve is antegrade and may be accomplished via entry into the left atrium by crossing the inter-atrial septum. In alternative arrangements, approach to the mitral valve can be retrograde where the left ventricle is entered through the aortic valve or via a transapical puncture. Once percutaneous access is achieved, the interventional tools and supporting catheter(s) may be advanced to the heart intravascularly and positioned adjacent the target cardiac valve in a variety of manners. For example, the heart valve prosthesis 100 may be delivered to a native mitral valve region for repair or replacement of the native valve via a transseptal approach (shown in FIGS. 10A-10D). Another suitable path to the native mitral valve may be made from the right atrium via a puncture through the intraventricular septum to gain access to the left ventricle. Suitable transatrial and/or transseptal implantation procedures that may be adapted for use with the heart valve prostheses 100 described herein are disclosed in U.S. Appl. Pub. No. 2011/0208297 to Tuval et al. and U.S. Appl. Pub. No. 2012/0035722 to Tuval et al, both of which are incorporated by reference herein in their entireties.

As is known in the art, a guidewire (not shown) may be advanced intravascularly using any number of techniques, e.g., through the inferior vena cava or superior vena cava (FIG. 1), into the right atrium RA through a penetration hole cut in the inter-atrial septum (not shown) and into the left atrium LA (FIG. 1). A guide catheter may be advanced along the guidewire and into the right atrium RA, through the penetration hole in the inter-atrial septum, and into the left atrium LA. The guide catheter may have a pre-shaped or steerable distal end to shape or steer the guide catheter such that it will direct a delivery catheter (not shown) toward the mitral valve MV.

Alternatively, the mitral valve may also be accessed via a transatrial approach for e.g., directly through an incision in the left atrium LA. Access to the heart may be obtained through an intercostal incision in the chest without removing ribs, and a guiding catheter may be placed into the left atrium LA through an atrial incision sealed with a pursestring suture. A delivery catheter may then be advanced through the guiding catheter to the mitral valve. Alternatively, the delivery catheter may be placed directly through the atrial incision without the use of a guiding catheter.

Figure 10A:
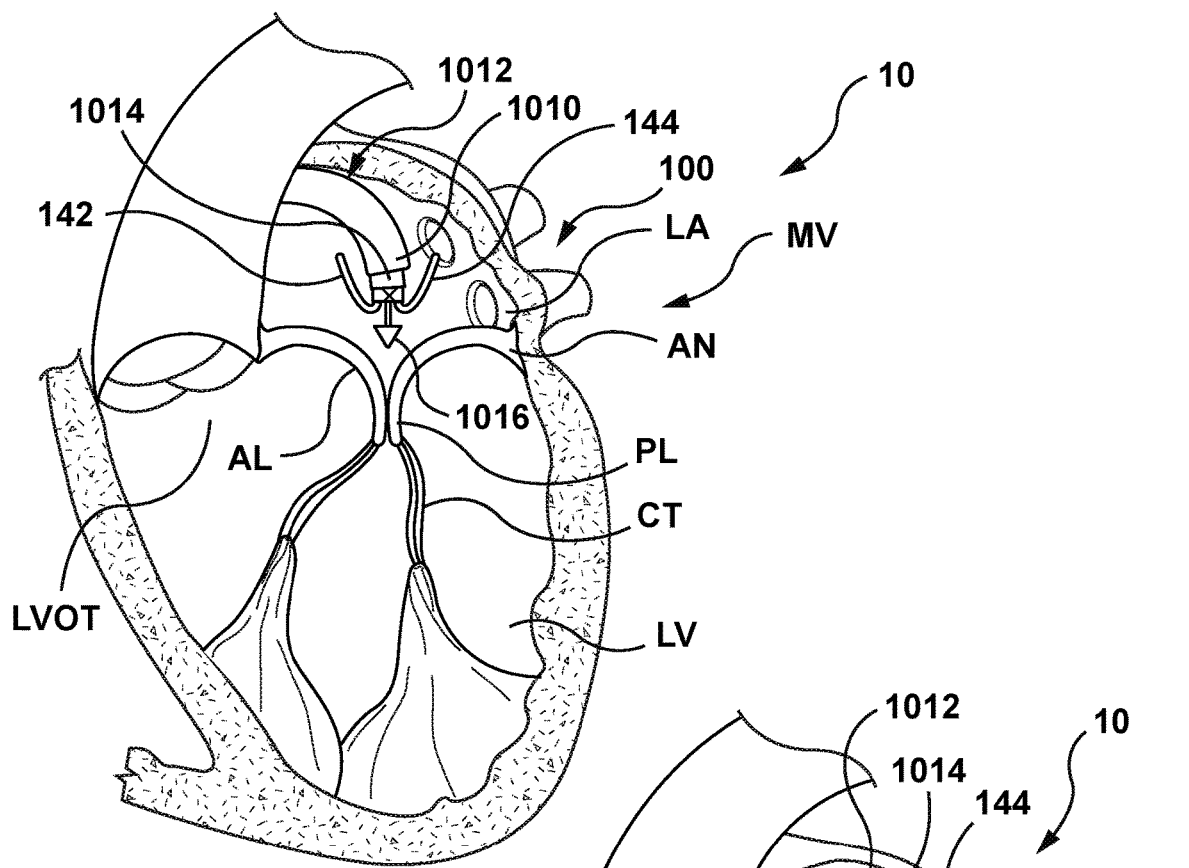
FIGS. 10A-10D are sectional views of the heart illustrating steps of a method of implanting a heart valve prosthesis using an antegrade or transseptal approach in accordance with another embodiment of the present technology.

FIGS. 10A-10D are schematic, sectional side views of a heart showing a trans-septal or antegrade approach for delivering and deploying a prosthetic heart valve device 100 in accordance with an embodiment of the present technology. Referring to FIGS. 10A-10D together, a distal end 1010 of a delivery catheter 1012 may be advanced into the left atrium LA and in general proximity to the mitral valve MV. Optionally, and as shown in FIG. 10A, a guidewire (not shown) may be used over which the delivery catheter 1012 may be slideably advanced. A delivery sheath 1014 of the delivery catheter 1012, which contains the prosthesis 100 in a radially compressed delivery configuration (FIG. 9), is at least partially retracted relative to a distal nose cone 1016 allowing the plurality of support arms 142, 144 to emerge and expand radially out and reflect back toward the upstream direction (FIG. 10A). In this deployment phase, the outward-to-upstream movement of the plurality of support arms 142, 144 from the straightened state shown in FIG. 9 to an expanded or relaxed state shown in FIGS. 4A-4B is facilitated by the shape-memory bias of the support arms 142, 144 and such movement of one or more of the plurality of support arms may occur in unison or consecutively depending on where the bend in the respective support arm occurs.

Image guidance, e.g., intracardiac echocardiography (ICE), fluoroscopy, computed tomography (CT), intravascular ultrasound (IVUS), optical coherence tomography (OCT), or another suitable guidance modality, or combination thereof, may be used to aid the clinician's positioning and manipulation of the prosthesis 100 at the target native valve region. For example, once the plurality of support arms 142, 144 are deployed within the left atrium LA with substantially a remainder of the prosthesis 100 still compressed in a delivery configuration within the delivery sheath 1014, such image guidance technologies can be used to aid in orienting the prosthesis 100 within the left atrium LA such that the main support arm 142 is aligned with the anterior leaflet, the first set of supplemental support arms 146 are aligned with the anterior leaflet AL at or proximate to the commissures, and the second set of supplemental support arms 148 are aligned with the posterior leaflet PL of the mitral valve MV. In some embodiments, image guidance components (e.g., IVUS, OCT) can be coupled to the distal portion of the delivery catheter 1012, guide catheter, or both to provide three-dimensional images of the area proximate to the target heart valve region to facilitate positioning, orienting and/or deployment of the prosthesis 100 within the heart valve region.

Figure 10B:
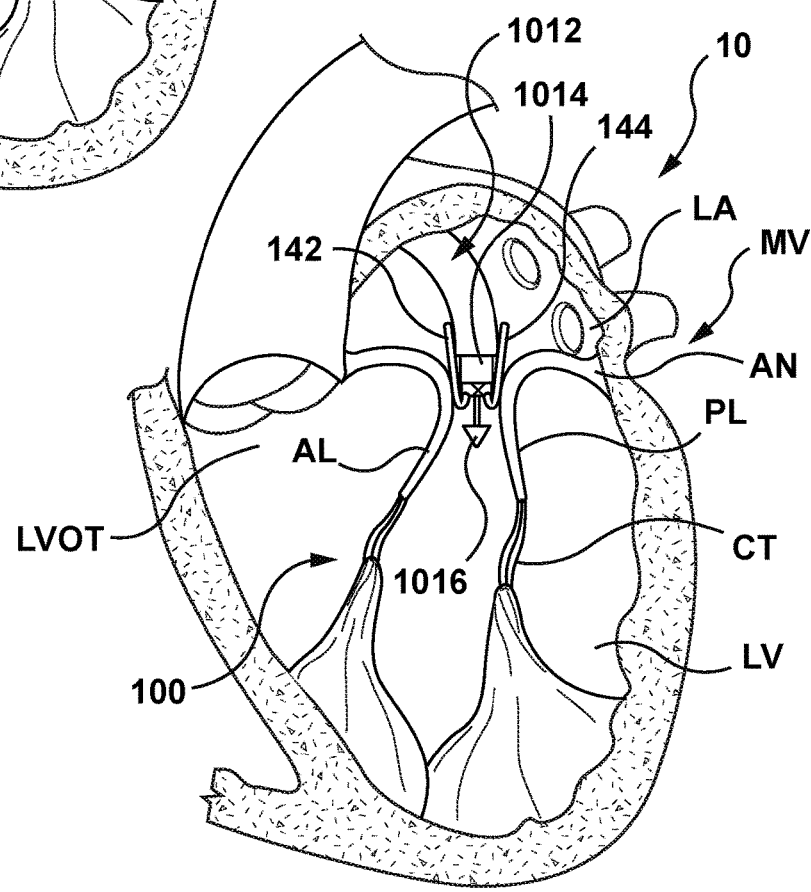

Once the plurality of support arms 142, 144 are deployed and oriented within the left atrium, the delivery catheter 1012 may again be advanced toward the mitral valve annulus AN until the plurality of support arms 142, 144 are pushed through the mitral valve annulus AN between native anterior and posterior leaflets AL, PL, as shown in FIG. 10B. In this delivery step, the support arms may compress or flex toward the delivery catheter 1012 while the delivery catheter advances through the mitral valve annulus AN before returning back to the original shape set position of the respective support arms (e.g., returning to its desired reflection angle). Once the delivery catheter 1012 has advanced the plurality of support arms 142, 144 through the annulus AN and into the left ventricle LV a suitable distance to situate the atraumatic end portions 143, 145 thereof within the left ventricle LV, the delivery catheter 1012 can be moved or retracted proximally in a retrograde direction such that the main support arm 142 captures the anterior leaflet AL and the end portions 145 of the supplemental support arms 144 come into contact and engage the subannular tissue.

Figure 10C:
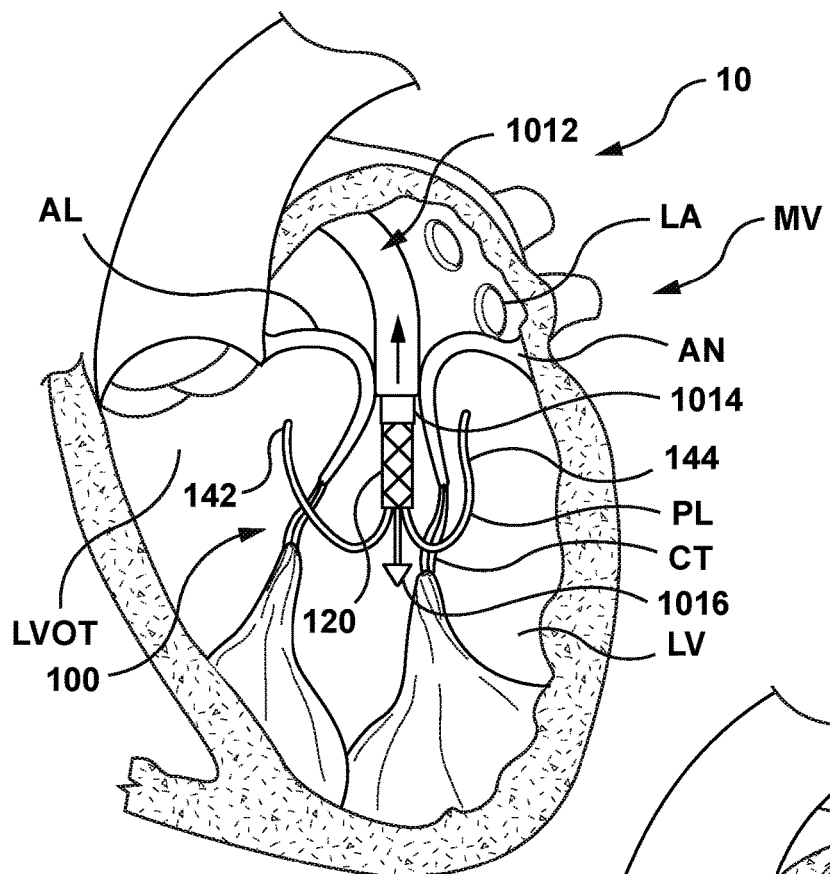
Figure 10D:
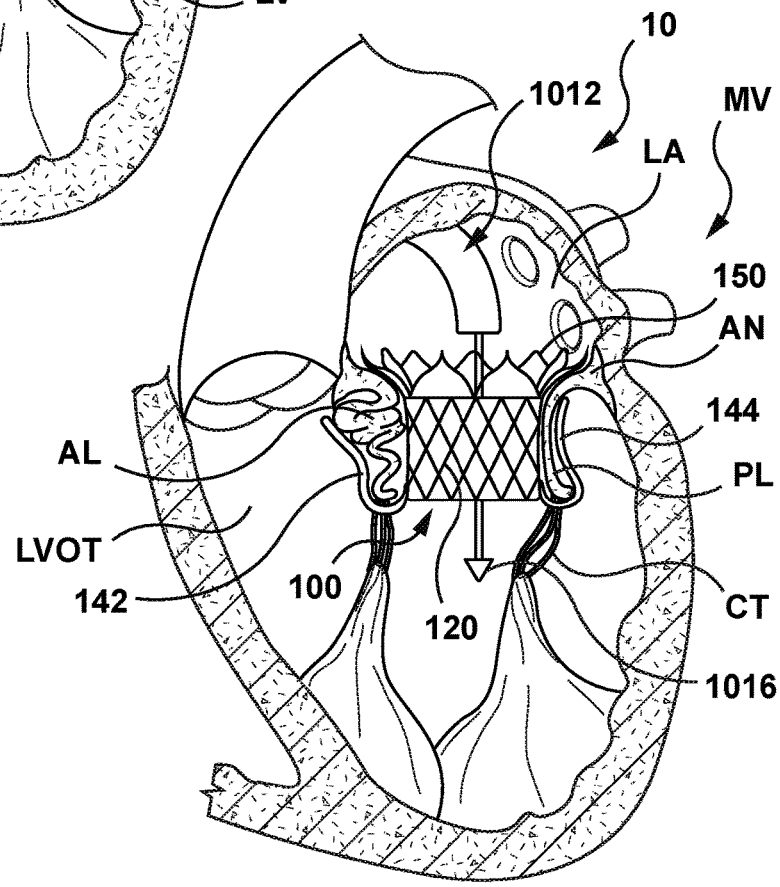

Referring to FIG. 10C, the delivery sheath 1014 is further retracted proximally allowing the prosthesis 100 to expand such that the valve support 120 pushes the leaflets AL, PL outwardly to fold beneath the mitral valve annulus AN and between the valve support 120 and the plurality of support arms 142, 144. The delivery sheath 1014 is fully removed and the radially-extending segment 150 is allowed to expand within the left atrium LA (FIG. 10D). During the delivery steps illustrated in FIGS. 10C and 10D, the delivery system can maintain retraction tension so that the supplemental support arms 144 continually maintain engagement with the subannular tissue. After the delivery sheath 1014 has been removed and the prosthesis 100 allowed to expand, the delivery system can still be connected to the prosthesis 100 via tethers (not shown) so that the operator can further control the placement of the prosthesis 100 as it expands toward the expanded configuration. Once the prosthesis 100 is positioned at the target site, the tethers (not shown) may be retracted in a proximal direction, to detach the prosthesis 100 in the deployed configuration from the delivery catheter 1012. The delivery catheter 1012 can then be removed and the prosthesis is deployed as shown in FIG. 6. Alternatively, the prosthesis 100 may not be connected to the delivery system via tethers such that the prosthesis 100 deploys and is fully released from the delivery system.

Figure 11:
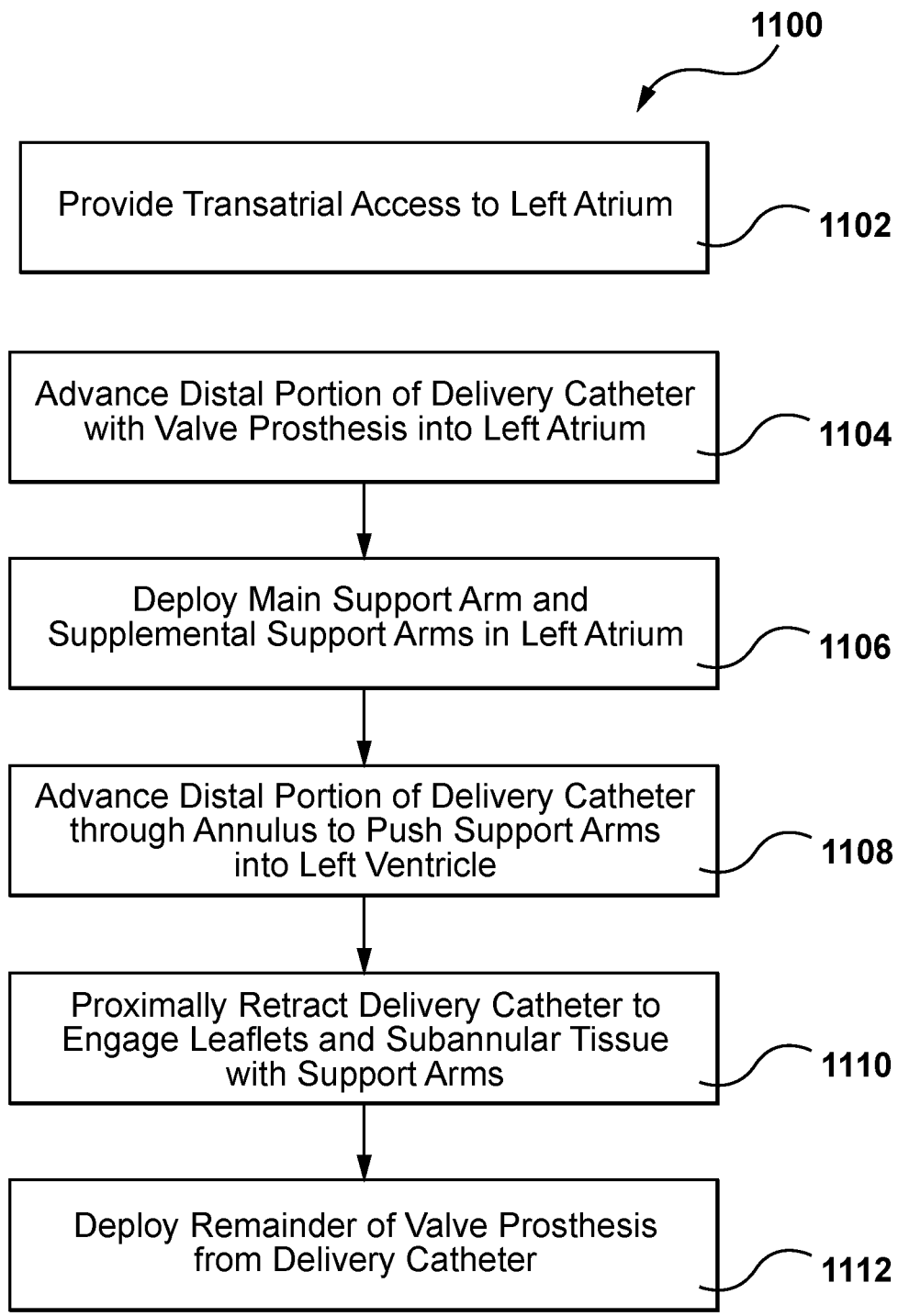
FIG. 11 is flow diagram illustrating a method for repairing or replacing a heart valve of a patient in accordance with an embodiment of the present technology.

FIG. 11 is block diagram illustrating a method 1100 for repairing or replacing a heart valve of a patient with the heart valve prosthesis 100 described above with reference to FIGS. 4A-10D and in accordance with an embodiment of the present technology. Referring to FIG. 11 (and with additional reference to FIGS. 4A-10D), the method 1100 can include providing transatrial access to the left atrium of the heart (block 1102). The method 1100 can also include advancing a distal portion of a delivery catheter 1012 having the heart valve prosthesis 100 in the compressed configuration therein into the left atrium LA via the transatrial access (block 1104). The prosthesis 100 includes the frame 110 having a main support arm 142 and a plurality of supplemental support arms 144. The method 1100 can also include deploying within the left atrium LA the main support arm 142 and the plurality of supplemental support arms 144 of the prosthesis 100 (block 1106). The main support arm 142 and each of the plurality of supplemental support arms 144 assumes a bent and upstream extending deployed state as it extends from the distal portion of the delivery catheter 1012 during this step.

At block 1108, the method 1100 can further include advancing the distal portion of the delivery catheter 1012 toward the annulus AN of the native mitral valve MV of the heart until the main support arm 142 and the plurality of supplemental support arms 144 in the bent and upstream extending deployed state are pushed through the annulus and into the left ventricle of the heart. The method 1100 continues at block 1110 with proximally retracting the delivery catheter until each of the main support arm 142 and the plurality of supplemental support arms 144 engages at least a portion of anterior and posterior leaflets AL, PL of the native mitral valve MV, with tips of a plurality of the supplemental support arms engaging the endocardial surface of the left ventricle near the mitral annulus. Accordingly, a primary fixation mechanism of a valve prosthesis in accordance herewith occurs between the supplemental support arm tips and the muscular portion of the annulus such that a mitral valve prosthesis hereof is much less dependent on capturing of the leaflets for anchoring versus known prosthetic mitral valve designs. The method 1100 further includes deploying the remainder of the prosthesis 100 from the delivery catheter 1012 to repair or replace the native mitral valve MV (block 1112).

Additional Embodiments

Features of the heart valve prosthesis and delivery system components described above and illustrated in FIGS. 4A-10D can be modified to form additional embodiments configured in accordance with the present technology. For example, the heart valve prosthesis described above and illustrated in FIGS. 4A-8C showing only a single main support arm or leaflet capture arm can also include additional leaflet capture arms extending from the valve support to, for example, capture posterior leaflet tissue and/or to further resist migration of the prosthesis following implantation. Various method steps described above for delivery and deployment of the heart valve prosthesis for repairing or replacing a heart valve of a patient also can be interchanged to form additional embodiments of the present technology. For example, while the method steps described above are presented in a given order, alternative embodiments may perform steps in a different order. The various embodiments described herein may also be combined to provide further embodiments.

While various embodiments have been described above, it should be understood that they have been presented only as illustrations and examples of the present technology, and not by way of limitation. It will be apparent to persons skilled in the relevant art that various changes in form and detail can be made therein without departing from the spirit and scope of the present technology. Thus, the breadth and scope of the present technology should not be limited by any of the above-described embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A method of deploying a valve prosthesis having a compressed configuration for delivery to a treatment site and an expanded configuration for deployment within a heart comprising:
   providing transatrial access to a left atrium of the heart;
   advancing a distal portion of a delivery catheter having the valve prosthesis in the compressed configuration therein into the left atrium via the transatrial access, wherein the valve prosthesis includes a frame having a main support arm and a plurality of supplemental support arms;
   deploying within the left atrium the main support arm and the plurality of supplemental support arms of the valve prosthesis such that the main support arm and each of the plurality of supplemental support arms assumes a bent deployed state as it extends from the distal portion of the delivery catheter;
   advancing the distal portion of the delivery catheter toward an annulus of a native mitral valve of the heart until the main support arm and the plurality of supplemental support arms in the bent deployed state are pushed through the annulus and into a left ventricle of the heart;
   proximally retracting the delivery catheter until each of the main support arm and the plurality of supplemental support arms engages at least a portion of an anterior leaflet of the native mitral valve or a portion of posterior leaflet of the native mitral valve; and
   deploying a remainder of the valve prosthesis from the delivery catheter to replace the native mitral valve.

2. The method of claim 1, further comprising:
   orienting the main support arm of the valve prosthesis with an A2 segment of the anterior leaflet of the native mitral valve prior to performing the step of advancing the distal portion of the delivery catheter toward an annulus of the native mitral valve.

3. The method of claim 2, wherein during the step of proximally retracting the delivery catheter the main support arm of the valve prosthesis is configured to engage and capture the anterior leaflet at the A2 segment prior to the plurality of supplemental support arms engaging remaining segments of the anterior leaflet or segments of the posterior leaflet.

4. The method of claim 1, wherein during the step of proximally retracting the delivery catheter end portions of the plurality of supplemental support arms are forced against the annulus and the force is maintained against the annulus while the step of deploying a remainder of the valve prosthesis is performed.

5. The method of claim 4, wherein the step of deploying a remainder of the valve prosthesis includes releasing within the left atrium an inlet section of the frame of the valve prosthesis to act against a floor of the left atrium in opposition to the plurality of supplemental support arms that act against an inferior side of the annulus to thereby anchor the valve prosthesis within the native mitral valve.

6. The method of claim 1,
wherein the frame further includes a tubular portion for retaining a prosthetic valve component therein, the tubular portion having a first end and a second end and an inflow portion that radially extends from the first end of the tubular portion when the valve prosthesis is in the expanded configuration,
wherein the main support arm extends from the second end of the tubular portion and has a first length, the main support arm including a first arm segment coupled to the second end of the tubular portion at a first attachment point and a second attachment point and the first arm segment defining a first loop between the first and second attachment points, the first length being defined between a terminal tip of the first loop and the first attachment point,
wherein the plurality of supplemental support arms include
a first set of supplemental support arms extending from the second end of the tubular portion, wherein each of the first set of supplemental support arms has a second length and wherein each of the first set of supplemental support arms includes a second arm segment coupled to the second end of the tubular portion at a third attachment point and a fourth attachment point and the second arm segment defines a second loop between the third and fourth attachment points, the second length being defined between a terminal tip of the second loop and the third attachment point, and
a second set of supplemental support arms extending from the second end of the tubular portion, wherein each of the second set of supplemental support arms includes a third arm segment coupled to the second end of the tubular portion at a fifth attachment point and a sixth attachment point and the third arm segment defines a third loop between the fifth and sixth attachment points, and wherein each of the second set of supplemental support arms has a third length that is less than the second length, the third length being defined between a terminal tip of the third loop and the fifth attachment point,
wherein the first length of the main support arm is longer than the respective second and third lengths of the supplemental support arms in the first and second sets of supplemental support arms.

7. The method of claim 6, wherein when the valve prosthesis is in the expanded configuration the main support arm and the first set of supplemental support arms engage the anterior leaflet of the native mitral valve and the second set of supplemental support arms engage the posterior leaflet of the native mitral valve.

8. The method of claim 6, wherein when the valve prosthesis is in the expanded configuration each of the supplemental support arms has substantially the same deployed height relative to the second end of the tubular portion of the frame such that the terminal tip of each supplemental support arm of the first set of supplemental support arms is at the same longitudinal position as the terminal tip of each supplemental support arm of the second set of supplemental support arms.

9. The method of claim 8, wherein when the valve prosthesis is in the expanded configuration each end portion of the supplemental support arms is disposed adjacent to an inflow portion of the frame so as to pinch tissue of the heart therebetween.

10. The method of claim 8, wherein the plurality of supplemental support arms include a first set of supplemental support arms and a second set of supplemental support arms, and wherein in the bent deployed state
a first angle is defined between the main support arm and a tubular portion of the frame,
a second angle is defined between each supplemental support arm of the first set of supplemental support arms and the tubular portion of the frame, and
a third angle is defined between each supplemental support arm of the second set of supplemental support arms and the tubular portion of the frame,
wherein the first angle is greater than the second angle and the second angle is greater than the third angle.

11. The method of claim 1, wherein in the bent deployed state the main support arm and the supplemental support arms bend toward an inflow portion of the frame.

12. A method of deploying a valve prosthesis having a compressed configuration for delivery to a treatment site and an expanded configuration for deployment within a heart comprising:
providing access to a left atrium of the heart;
advancing a distal portion of a delivery catheter having the valve prosthesis in the compressed configuration therein into the left atrium via the access, wherein the valve prosthesis includes a frame having
a valve support with a first end and a second end,
an inflow portion that radially extends from the first end of the valve support when the valve prosthesis is in the expanded configuration,
a main support arm extending from the second end of the valve support and having a first length, wherein the main support arm includes a first arm segment coupled to the second end of the valve support at a first attachment point and a second attachment point and the first arm segment defines a first loop between the first and second attachment points, the first length being defined between a terminal tip of the first loop and the first attachment point,
a plurality of tall supplemental support arms extending from the second end of the valve support, wherein each of the tall supplemental support arms has a second length and wherein each of the tall supplemental support arms includes a second arm segment coupled to the second end of the valve support at a third attachment point and a fourth attachment point and the second arm segment defines a second loop between the third and fourth attachment points, the second length being defined between a terminal tip of the second loop and the third attachment point, and
a plurality of short supplemental support arms extending from the second end of the valve support, wherein each of the short supplemental support arms has a third length and wherein each of the short supplemental support arms includes a third arm segment coupled to the second end of the valve support at a fifth attachment point and a sixth attachment point and the third arm segment defines a third loop between the fifth and sixth attachment points, the third length being defined between a terminal tip of the third loop and the fifth attachment point, and wherein the first length of the main support arm is longer than the respective second and third lengths of the pluralities of tall and short supplemental support arms, and deploying within the left atrium the main support arm, the plurality of tall supplemental support arms, and the plurality of short supplemental support arms of the valve prosthesis such that the main support arm and each of the plurality of tall and short supplemental support arms assumes a bent deployed state as it extends from the distal portion of the delivery catheter, wherein in the bent deployed state the main support arm, the plurality of tall supplemental support arms and the plurality of short supplemental support arms bend toward the first end of the valve support, and advancing the distal portion of the delivery catheter toward an annulus of a native mitral valve of the heart until the main support arm, the plurality of tall supplemental support arms, and the plurality of short supplemental support arms in the bent deployed state are pushed through the annulus and into a left ventricle of the heart;

proximally retracting the delivery catheter until each of the main support arm and the plurality of tall and short supplemental support arms engages at least a portion of an anterior leaflet of the native mitral valve or a portion of posterior leaflet of the native mitral valve; and deploying a remainder of the valve prosthesis from the delivery catheter to replace the native mitral valve.

13. The method of claim 12, further comprising:
orienting the main support arm of the valve prosthesis with an A2 segment of the anterior leaflet of the native mitral valve prior to performing the step of advancing the distal portion of the delivery catheter toward an annulus of the native mitral valve.

14. The method of claim 13, wherein during the step of proximally retracting the delivery catheter the main support arm of the valve prosthesis is configured to engage and capture the anterior leaflet at the A2 segment prior to the plurality of tall and short supplemental support arms engaging remaining segments of the anterior leaflet or segments of the posterior leaflet.

15. The method of claim 14, wherein during the step of proximally retracting the delivery catheter end portions of the plurality of tall and short supplemental support arms are forced against the annulus and the force is maintained against the annulus while the step of deploying a remainder of the valve prosthesis is performed.

16. The method of claim 15, wherein the step of deploying a remainder of the valve prosthesis includes releasing within the left atrium the inflow portion of the frame of the valve prosthesis to act against a floor of the left atrium in opposition to the plurality of tall and short supplemental support arms that act against an inferior side of the annulus to thereby anchor the valve prosthesis within the native mitral valve.

17. The method of claim 12, wherein when the valve prosthesis is in the expanded configuration each of the plurality of tall supplemental support arms and each of the plurality of short supplemental support arms has substantially the same deployed height relative to the second end of the valve support such that the terminal tip of the third loop of each short supplemental support arm is at the same longitudinal position as the terminal tip of the second loop of each long supplemental support arm.

18. The method of claim 17, wherein when the valve prosthesis is in the expanded configuration the terminal tips of the tall and short supplemental support arms are disposed adjacent to the inflow portion of the frame so as to pinch annular tissue of the heart therebetween.

19. The method of claim 17, wherein when the valve prosthesis is in the expanded configuration
a first angle is defined between the main support arm and the tubular portion of the frame,
a second angle is defined between each supplemental support arm of the tall supplemental support arms and the tubular portion of the frame, and
a third angle is defined between each supplemental support arm of the short supplemental support arms and the tubular portion of the frame,
wherein the first angle is greater than the second angle and the second angle is greater than the third angle.

20. The method of claim 12, wherein when the valve prosthesis is in the expanded configuration the main support arm and the plurality of tall supplemental support arms engage the anterior leaflet of the native mitral valve and the plurality of short supplemental support arms engage the posterior leaflet of the native mitral valve.

\* \* \* \* \*